[12] United States Patent
Andrews et al.

(10) Patent No.: US 6,860,976 B2
(45) Date of Patent: Mar. 1, 2005

(54) ELECTROCHEMICAL APPARATUS WITH RETRACTABLE ELECTRODE

(75) Inventors: Craig C. Andrews, College Station, TX (US); Oliver J. Murphy, Bryan, TX (US); Brian Boyd, Fort Collins, CO (US)

(73) Assignee: Lynntech International, Ltd., College Station, TX (US)

( * ) Notice: Subject to any disclaimer, the term of this patent is extended or adjusted under 35 U.S.C. 154(b) by 183 days.

(21) Appl. No.: 10/016,482

(22) Filed: Dec. 10, 2001

(65) Prior Publication Data

US 2002/0134674 A1 Sep. 26, 2002

Related U.S. Application Data

(63) Continuation-in-part of application No. 09/598,067, filed on Jun. 20, 2000, now Pat. No. 6,365,026.
(60) Provisional application No. 60/254,820, filed on Dec. 12, 2000, provisional application No. 60/261,101, filed on Jan. 10, 2001, provisional application No. 60/261,534, filed on Jan. 12, 2001, and provisional application No. 60/317,562, filed on Sep. 5, 2001.

(51) Int. Cl.$^7$ .............................................. C25D 17/00
(52) U.S. Cl. ...................................... 204/225; 204/263
(58) Field of Search ................................. 204/225, 263

(56) References Cited

U.S. PATENT DOCUMENTS

| 2,925,371 A | | 2/1960 | Van Winckel et al. | |
| 4,078,987 A | * | 3/1978 | Specht | 204/266 |
| 4,416,747 A | | 11/1983 | Menth et al. | |
| 4,500,401 A | * | 2/1985 | Clark et al. | 204/225 |
| 4,759,847 A | | 7/1988 | Medbury | |
| 4,759,849 A | | 7/1988 | Baumann et al. | |

(List continued on next page.)

FOREIGN PATENT DOCUMENTS

| EP | 0 048 559 | 9/1980 |
| EP | 0 342 169 A2 | 5/1989 |
| EP | 0 342 169 | 5/1989 |
| EP | 0 711 731 A2 | 5/1996 |
| EP | 0 711 731 A3 | 2/1997 |
| EP | 196 53 034 A 1 | 7/1998 |
| EP | 0 822 271 A3 | 9/1998 |
| EP | 1 038 993 A1 | 9/2000 |
| JP | 01183071 | 7/1989 |
| JP | PCT/JP01/007 | 5/2001 |
| WO | WO 90/14312 | 11/1990 |
| WO | WO 94/07802 | 4/1994 |
| WO | WO 95/16730 | 6/1995 |
| WO | WO 01/61074 A1 | 2/2001 |
| WO | WO 01/35755 A1 | 5/2001 |

OTHER PUBLICATIONS

M. Pourbaix, N. De Zoubov, C. Vanleugenhaghe & P. Van Rysselberghe, Lead 1, Section 17.5 pp. 485–492 (No Date).

*Primary Examiner*—Donald R. Valentine
(74) *Attorney, Agent, or Firm*—Streets & Steele; Jeffrey L. Streets; Frank J. Campigotto

(57) ABSTRACT

Electrochemical apparatus and methods that support periodic, non-steady state, or discontinuous operation without suffering degradation of materials or loss of efficiency. The invention provides a means for positioning one or more electrodes into contact with electrolyte and means for retracting the one or more electrodes out of contact with the electrolyte. The means for positioning and means for retracting may be the same device or different devices. The means for positioning and means for retracting may be designed to provide automatic, passive, or fail-safe retraction of the electrode upon a given shutdown condition, such as a voltage of less than one Volt being applied between the first and second electrodes, expiration of a time period, an ozone concentration greater than a setpoint ozone concentration, contact pressure of less than 5 psig, and combinations thereof.

191 Claims, 23 Drawing Sheets

U.S. PATENT DOCUMENTS

| | | |
|---|---|---|
| 4,836,929 A | 6/1989 | Baumann et al. |
| 4,978,438 A | 12/1990 | Shimamune |
| 5,083,442 A | 1/1992 | Vlock |
| 5,094,734 A | 3/1992 | Torrado |
| 5,097,556 A | 3/1992 | Engel et al. |
| 5,114,549 A | 5/1992 | Shimamune et al. |
| 5,158,454 A | 10/1992 | Viebahn et al. |
| 5,290,406 A | 3/1994 | Sawamoto et al. |
| 5,372,689 A | 12/1994 | Carlson et al. |
| 5,433,866 A | 7/1995 | Hoppe et al. |
| 5,460,705 A | 10/1995 | Murphy et al. |
| 5,529,683 A | 6/1996 | Critz et al. |
| 5,547,551 A | 8/1996 | Bahar et al. |
| 5,547,584 A | 8/1996 | Capehart |
| 5,582,717 A | 12/1996 | Si Santo |
| 5,589,052 A | 12/1996 | Shimamune et al. |
| 5,607,562 A | 3/1997 | Shimamune et al. |
| 5,626,769 A | 5/1997 | Sawamoto |
| 5,683,576 A | 11/1997 | Olsen |
| 5,753,100 A | 5/1998 | Lumsden |
| 5,766,488 A | 6/1998 | Uban et al. |
| 5,779,865 A | 7/1998 | Schulze et al. |
| 5,824,274 A | 10/1998 | Long |
| 5,989,407 A | 11/1999 | Andrews et al. |
| 5,997,702 A | 12/1999 | Koganezawa et al. |
| 6,042,958 A | 3/2000 | Denton et al. |
| 6,074,551 A | 6/2000 | Jones et al. |
| 6,200,618 B1 | 3/2001 | Smith et al. |
| 6,299,998 B1 | 10/2001 | Morris |
| 2002/0139690 A1 | 10/2002 | Kanaya et al. |

* cited by examiner

ELECTROCHEMICAL APPARATUS WITH RETRACTABLE ELECTRODE

This nonprovisional application is a continuation-in-part application of U.S. nonprovisional application Ser. No. 09/598,067 filed on Jun. 20, 2000, now U.S. Pat. No. 6,365,026 and claims priority of U.S. provisional application No. 60/254,820 filed on Dec. 12, 2000, U.S. provisional application No. 60/261,101 filed on Jan. 10, 2001, U.S. provisional application No. 60/261,534 filed on Jan. 12, 2001, and U.S. provisional application No. 60/317,562 filed on Sep. 5, 2001.

BACKGROUND OF THE INVENTION

1. Field of the Invention

This invention relates to an electrochemical apparatus capable of periodic operation without suffering long-term loss of efficiency or degradation of materials, in particular electrocatalyst layers or coatings.

2. Background of the Related Art

Ozone is known to be a powerful oxidizing species. Numerous methods and apparatus have been used to generate ozone and use ozone. However, many potential applications for the use of ozone do not require, or cannot utilize, a continuous stream of ozone gas or ozonated water. Unfortunately, the generation and use of ozone in discontinuous, unsteady-state, or batch modes of operation can be problematic for a variety of reasons. First, the high reactivity and rapid decomposition of ozone necessitate that the ozone be generated just prior to utilization. This dictates that ozone-generating capacity must closely match the peak rate of consumption. Second, the need to generate highly concentrated ozone favors electrochemical processes, most preferably using a lead dioxide anodic electrocatalyst.

While lead dioxide ($PbO_2$) is generally unstable in aqueous acid solutions, the potential-pH equilibrium diagram for lead-water at 25° C. in FIG. 1 shows that maintaining a high positive electrode potential, with respect to the standard hydrogen electrode (SHE), on the positive $PbO_2$ electrode in an electrochemical apparatus can stabilize lead dioxide. Therefore, lead dioxide instability in acid solutions is easily avoided in continuous electrochemical processes since a relatively high electrical potential is continuously maintained across the positive and negative electrodes. Where the electrochemical process is needed only periodically, it is possible to reduce the rate of the electrochemical process while supplying a lower electrical potential across the positive and negative electrodes, which stabilizes the lead dioxide by maintaining a trickle of electrical current between the electrodes. Unfortunately, continuous electrochemical processes and continuous electrical potentials are not practical in numerous applications, such as residential or consumer products, since power outages and even drained backup batteries can be experienced. Yet another possible solution is to use platinum metal as the anode electrocatalyst, but the penalty for using platinum is a lower ozone yield and higher cost.

Central to the operation of any electrochemical cell is the occurrence of oxidation and reduction reactions that produce or consume electrons. These reactions take place at electrode/solution interfaces, where the electrodes must be good electronic conductors. In operation, a cell is connected to an external load or to an external voltage source, and electrons transfer electric charge between the anode and the cathode through the external circuit. To complete the electric circuit through the cell, an additional mechanism must exist for internal charge transfer. Internal charge transfer is provided by one or more electrolytes, which support charge transfer by ionic conduction. Electrolytes must be poor electronic conductors to prevent internal short-circuiting of the cell.

The simplest electrochemical cell consists of at least two electrodes and one or more electrolytes. The electrode at which the electron producing oxidation reaction occurs is the anode. The electrode at which an electron consuming reduction reaction occurs is called the cathode. The direction of the electron flow in the external circuit is always from anode to cathode.

Electrochemical cells in which a chemical reaction is forced by added AC/DC electrical energy are called electrolytic cells. Electrochemical cells also include fuel cells, which are supplied with fuel to bring about the generation of DC current, and batteries, such as zinc/manganese dioxide.

The electrolyte may be a liquid electrolyte (aqueous or organic solvent, with a dissolved salt, acid or base) or a solid electrolyte, such as a polymer-based ion exchange membrane that can be either a cation exchange membrane (such as a proton exchange membrane, PEM) or an anion exchange membrane. The membrane may also be a ceramic based membrane, such as ytria-stabilized zirconia which is an $O^{-2}$ ionic conductor.

However, ozone ($O_3$) may be produced by an electrolytic process, wherein an electric current (normally D.C.) is impressed across electrodes immersed in an electrolyte. The electrolyte includes water that dissociates into its respective elemental species, $O_2$ and $H_2$. Under suitable conditions, the oxygen is also evolved as the $O_3$ species. The evolution of oxygen and ozone at the anode may be represented as:

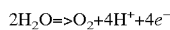
$$2H_2O => O_2 + 4H^+ + 4e^-$$

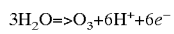
$$3H_2O => O_3 + 6H^+ + 6e^-$$

Utilization of high overpotentials, such as anode potentials greater than 1.57 Volts, and certain electrocatalyst materials enhance ozone formation at the expense of oxygen evolution. The water oxidation reactions yield protons and electrons which are recombined at the cathode. Electrons are conducted to the cathode via the external electronic circuit. The protons are carried through a solid electrolyte, such as a proton exchange membrane (PEM).

The cathodic reactions may utilize hydrogen formation:

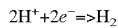
$$2H^+ + 2e^- => H_2$$

or involve the reduction of oxygen as follows:

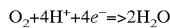
$$O_2 + 4H^+ + 4e^- => 2H_2O$$

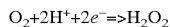
$$O_2 + 2H^+ + 2e^- => H_2O_2$$

Specialized gas diffusion electrodes are required for the oxygen reduction reaction to occur efficiently. The presence of oxygen at the cathode suppresses the hydrogen formation reaction. Furthermore, the oxygen reactions are thermodynamically favored over hydrogen formation. In this manner, the reduction of oxygen to either water or hydrogen peroxide reduces the overall cell voltage below that required to evolve hydrogen.

Therefore, there is a need for an electrochemical apparatus and methods that support periodic, non-steady state, or discontinuous operation without suffering degradation of materials, including electrocatalysts, or loss of efficiency. It would be desirable if the apparatus and methods did not require operator attention to verify the status of the power supply. It would also be desirable if the apparatus and methods support large amounts of repetitive use at various operating and standby durations and frequencies.

SUMMARY OF THE INVENTION

The present invention provides an electrochemical apparatus comprising an electrochemical cell having first and second electrodes and electrolyte, such as an ion exchange membrane, disposed between the first and second electrodes, a power source for applying a voltage between the first and second electrodes, and means for automatically retracting one or more of the first and second electrodes out of contact with the electrolyte. Optionally, the means for automatically retracting may be passive, and the passive means for repetitively retracting may be a stored energy device. A stored energy device may be selected from a spring, gravity, hydraulic accumulator, pneumatic accumulator, or combinations thereof.

The invention is well suited for use with one or more of the first and second electrodes includes material, such as lead dioxide, that is unstable or deactivates in the presence of the electrolyte without applying a voltage. The invention is characterized in that the lead dioxide maintains its activity during repetitive cycling of the power source.

The electrochemical apparatus may further comprise a pump for delivering water to the electrochemical cell, wherein the means for retracting is a hydraulic actuator in fluid communication with the water. Preferably, the electrolyte, such as an ion exchange membrane, and one of the electrodes, most preferably the cathode, are stationary. Where a lead-dioxide electrocatalyst is used, it may be desirable to include a lead removal device in fluid communication with the electrochemical cell, wherein the lead removal device contains a material known to bind or adsorb lead ions, particulates or colloidal species. Such lead removal material may be selected from a zeolite, alumina, silica, or mixtures thereof, and may be in powdered or granulated form.

In a preferred embodiment, the one or more of the first and second electrodes are retracted out of contact with the electrolyte when no voltage is being applied between the first and second electrodes. The means for retracting the one or more electrodes may also include a guide member to align the electrodes.

The electrochemical apparatus preferably also has a means for positioning the first and second electrodes in contact with the electrolyte. Preferably, the electrolyte is an ion exchange membrane, the first electrode is coupled to the means for positioning, and the first electrode has an electrocatalyst formed only on surfaces of the first electrode that are disposed to make contact with the ion exchange membrane. In one embodiment, the second electrode is stationary and the ion exchange membrane is secured onto the second electrode.

Exemplary means for positioning are selected from a hydraulic actuator, a pneumatic actuator, manual mechanical means, piezo-electric means, electric motor means, or combinations thereof, and preferably provide a compressive force against the ion exchange membrane generally between 5 and 100 psig, most preferably greater than 15 psig. The apparatus maybe designed so that the means for retracting overcomes the means for positioning when the power source is off, or so that the means for positioning overcomes the means for retracting when the power source is on.

The present invention also provides a method of operating an electrochemical cell having first and second electrodes and electrolyte disposed between the first and second electrodes, comprising automatically separating one or more of the first and second electrodes from the electrolyte upon one or more standby conditions. The one or more standby conditions may be selected from, but not limited to, a voltage of less than one Volt being applied between the first and second electrodes, expiration of a time period, an ozone concentration greater than a setpoint ozone concentration, contact pressure of less than 10 psig, or combinations thereof. Furthermore, the method may include automatically positioning the one or more of the first and second electrodes into contact with the electrolyte upon one or more production conditions. The one or more production conditions may be selected from a voltage greater than one Volt being applied between the first and second electrodes, expiration of a time period, an ozone concentration less than a setpoint ozone concentration, contact pressure greater than 10 psig, or combinations thereof.

The preferred electrolyte is a polymer electrolyte membrane, and the step of automatically positioning preferably comprises compressing the one or more of the first and second electrodes against the polymer electrolyte membrane with a compressive force between 5 and 100 psig, most preferably between 25 and 70 psig. While the method steps disclosed herein should generally not be limited to taking the steps in a given order, it is important when using a lead dioxide electrocatalyst, to apply a voltage between the first and second electrodes before positioning the one or more of the first and second electrodes into contact with the electrolyte upon one or more production conditions.

BRIEF DESCRIPTION OF THE DRAWINGS

So that the above recited features and advantages of the present invention can be understood in detail, a more particular description of the invention, briefly summarized above, may be had by reference to the embodiments thereof that are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Figure 1:
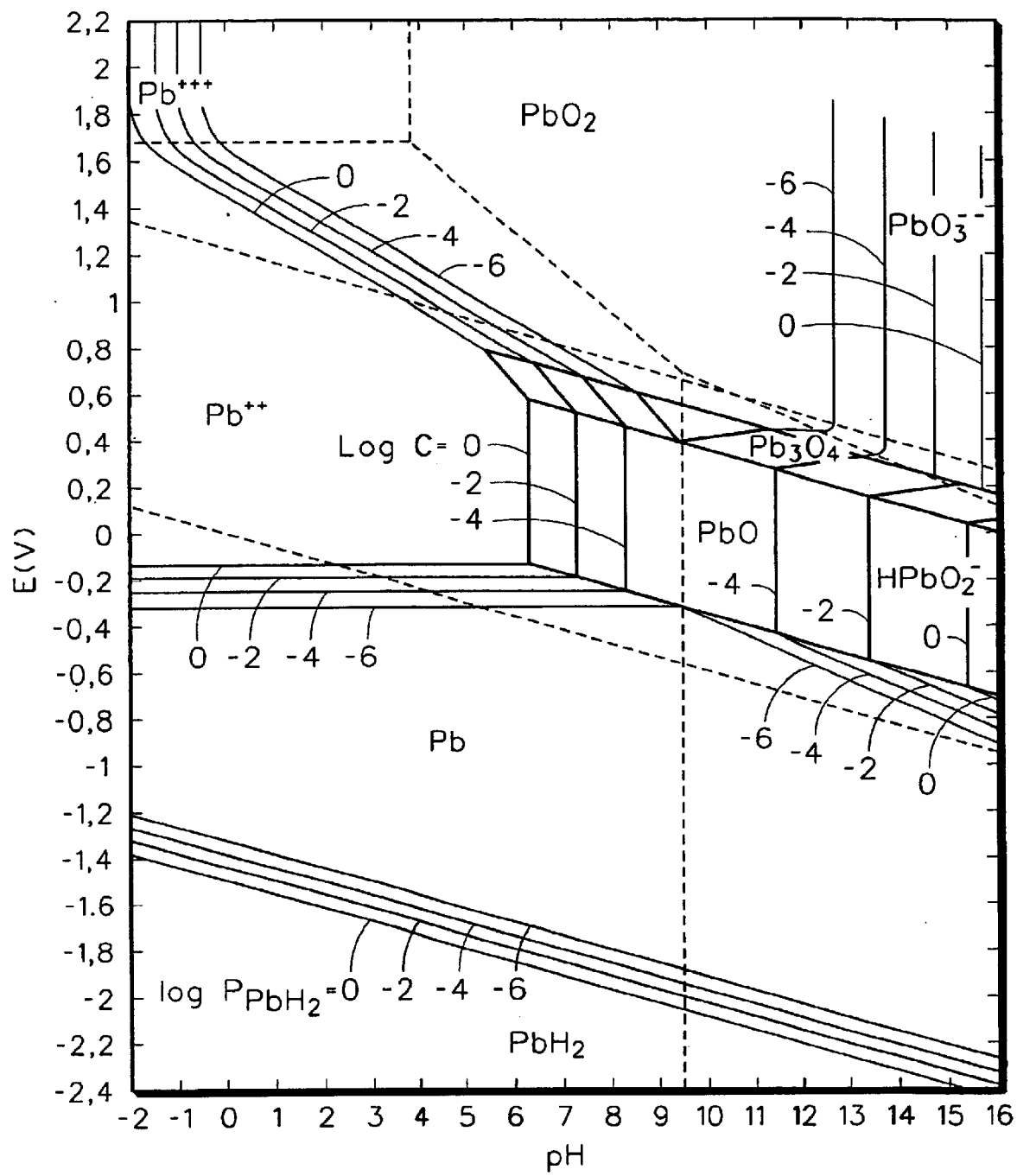
FIG. 1 is a potential-pH equilibrium diagram for the system of lead-water at 25° C.

The present invention provides electrochemical apparatus and methods that support periodic, non-steady state, or discontinuous operation without suffering degradation of materials, including electrocatalysts, or loss of efficiency. The apparatus and methods do not require operator attention to verify that an electrical potential across the positive and negative electrodes, otherwise referred to as a cell voltage, is continuously applied to the cell. The apparatus and methods support large amounts of repetitive "on"/"off" cycles at various operating and standby durations and frequencies.

The basic structural unit of the electrochemical apparatus is an electrochemical cell. Thus, an electrochemical apparatus can consist of a single electrochemical cell or a plurality of electrochemical cells, either stacked in series in a bipolar filter press configuration or stacked in series and electrically connected in a monopolar format. The structural elements of an electrochemical cell consist of an anode, or positive electrode, separated from a cathode, or negative electrode, by an ionically conducting electrolyte. If the electrolyte is a liquid, a microporous separator may also be placed between the anode and cathode. The positive and negative electrodes are held spaced apart from each other and contained, along with the electrolyte, in a container having walls which provide support and containment for the elements identified. The container also may have a plurality of input and output ports associated with the supply of reactants and withdrawal of products from both the anodic region of the container as well as the cathodic region of the container.

The anodic and cathodic electrodes may consist of a substrate material on which is coated a suitable electrocatalyst layer. However, the substrate material may also function as the electrocatalyst itself. For many electrochemical processes, it is most suitable that the electronically conducting anodic and cathodic electrode substrates should be porous to allow access of liquid or gaseous reactants to the electrocatalyst/electrolyte interface or withdrawal of liquid or gaseous products from the electrocatalyst/electrolyte interface.

Suitable anodic electrode substrates that are capable of withstanding high positive electrode potentials, aggressive electrolytes (concentrated aqueous mineral acids and mineral bases), and highly oxidizing environments (ozone evolution) include porous titanium, porous titanium suboxides (such as that produced by Atraverda Limited under the trademark "EBONEX"), porous platinum, porous tungsten, porous tantalum, porous hafnium, porous niobium, porous zirconium, and combinations thereof. The porous anodic substrates could be in the form of sintered powders or particles, compressed and sintered, or just compressed randomly oriented fibers, woven or non-woven cloth or mesh, screens, felt materials, highly perforated metal sheets, or metal sheets with microetched holes. In the case of electrochemical ozone evolution, suitable anodic electrocatalyst layers include α-lead dioxide, β-lead dioxide, boron-doped diamond, platinum-tungsten alloys or mixtures, glassy carbon, fluorinated graphite, and platinum.

Suitable cathodic electrode substrates or suitable cathodic electrode backing materials include porous metals selected from stainless steels (in particular, 304 stainless steel and 316 stainless steel), nickel, nickel-chromium alloys, copper, titanium, titanium suboxides, tantalum, hafnium, niobium and zirconium. These cathodic substrates should be porous to allow the supply of liquid or gaseous reactants to the cathodic electrocatalyst/electrolyte interface or withdrawal of liquid or gaseous products from the cathodic electrocatalyst/electrolyte interface. Suitable porous cathodic substrates include sintered powders or particles, compressed and sintered or just compressed randomly oriented fibers, woven or non-woven cloth or mesh, screens, felts, highly perforated metal sheets, or metal sheets with microetched holes. In the case of electrochemical evolution of ozone, a most suitable cathodic electrode substrate or electrode backing material can be derived from porous stainless steel materials. Preferred cathodic electrocatalyst layers include platinum, palladium, gold, iridium, nickel, pyrolyzed carbon-supported cobalt phthalocyanine, graphite or carbon materials, ruthenium oxide, iridium oxide, ruthenium/iridium oxide, ruthenium/iridium/titanium oxide, carbon-supported platinum, carbon-supported palladium, and mixtures thereof.

Alternatively, the cathode may be a gas diffusion cathode, for example comprising a polytetrafluoroethylene-bonded, semi-hydrophobic catalyst layer supported on a hydrophobic gas diffusion layer. In one embodiment of the present invention, the catalyst layer is comprised of a proton exchange polymer, polytetrafluoroethylene polymer and an electrocatalyst selected from platinum, palladium, gold, iridium, nickel, pyrolyzed carbon-supported cobalt phthalocyanine, graphite or carbon materials, ruthenium oxide, iridium oxide, ruthenium/iridium oxide, ruthenium/iridium/titanium oxide, carbon-supported platinum, carbon-supported palladium, and mixtures thereof. The gas diffusion layer has a carbon cloth or carbon paper fiber impregnated with a sintered mass derived from fine carbon powder and a polytetrafluoroethylene emulsion. This and other gas diffusion cathodes are suitable for air depolarization of the cathode, particularly in regard to open cathodes. U.S. Pat. Nos. 5,770,033 and 5,972,196 are incorporated by reference herein.

Electrolytes that are particularly useful in electrochemical cells comprise aqueous solutions of mineral acids, aqueous solutions of bases, aqueous solutions of salts, or aqueous solutions of salts combined with either acids or bases. For the electrochemical production of ozone in an electrolytic cell, it is particularly advantageous to use an electrolyte consisting of water and the acids or salts of fluoroanions dissolved therein. The fluoroanion electrolytes are capable of producing high yields of ozone. Fluoroanions and in particular the hexafluoro-anions, are especially preferred. Aqueous fluoroanion-containing electrolytes are described in U.S. Pat. No. 4,316,782, which patent is incorporated by reference herein.

A particular class of electrolytes suitable for use in accordance with this invention may be any number of ion exchange polymers including polymers with cation exchange groups that are preferably selected from the group consisting of sulfonate, carboxylate, phosphonate, imide, sulfonimide, and sulfonamide groups. Various known cation exchange polymers can be used including polymers and co-polymers of trifluoroethylene, tetrafluoroethylene, styrene-divinylbenzene, $\alpha$-, $\beta_1$-, $\beta_2$-trifluorostyrene, etc., in which cation exchange groups have been introduced. Polymeric electrolytes for use in accordance with the present invention are preferably highly fluorinated ion-exchange polymers having sulfonate ion exchange groups. "Highly fluoroinated" means that at least 90% of the total number of univalent atoms in the polymer are fluorine atoms. Most preferably, the polymer is perfluorinated sulfonic acid. Suitable solid polymer electrolytes based on ion exchange polymers are described in U.S. Pat. No. 6,110,333 and 6,042,958, which patents are incorporated by reference herein. Solid polymer electrolytes based on perfluorinated cation exchange polymers are most suitable for electrochemical ozone evolution. This is because only water, free of dissolved ionic species or suspended inorganic or organic materials, needs to be added to an electrochemical cell. This avoids the degradation of electrochemical cell components by aggressive electrolytes and the entrainment of liquid electrolytes in evolved gaseous ozone.

It is particularly preferred to utilize an ion exchange polymer that is reinforced to improve the integrity and durability of the membrane. In particular, ultra-thin composite membranes below 50 $\mu$m in thickness and comprising proton exchange polymers incorporated into an expanded porous polytetrafluoroethylene (PTFE) membrane are suitable for use as the polymer electrolyte in the present invention. Such expanded PTFE-reinforced membranes are described in U.S. Pat. No. 5,547,551 assigned to W.L. Gore & Associates Inc., which patent is hereby incorporated by reference. Another suitable membrane includes a porous substrate of randomly orientated individual fibres and an ion conducting polymer embedded within the porous substrate. This individual fiber reinforced membrane is described in U.S. Pat. No. 6,042,958, which patent is hereby incorporated by reference. Other reinforced membranes that are currently available or that will be developed in the future may also be suitable for use in accordance with the invention.

The proton exchange membrane placed between the anode and cathode is made of a polymer material having sulfonate functional groups contained on a fluorinated carbon backbone. Two such materials include a "NAFION" PEM having an equivalent weight of 1100 grams and a Dow experimental PEM (XUS-13204.20) having an equivalent weight of 800 grams. While "NAFION" 105, 115 and 117 will each operate satisfactorily in the present invention, "NAFION" 117 is the preferred "NAFION" product. However, it is anticipated that a sulfonated polymer having a nonfluorinated carbon backbone would be operable according to the present invention. Such a polymer might include polystyrene sulfonate. Additionally, such a material might be coated with a fluorinated material to increase its resistance to chemical attack. It is also anticipated that a proton exchange membrane made of a polymer material having carboxylate functional groups attached to a fluorinated carbon backbone would be operable according to the present invention. Examples include those available from Tokuyama Soda Company under the trademark "NEOSEPT-F", Asahi Glass Company under the trademark "FLEMION", Asahi Chemical Industry Company under the trademark "ACIPLEX-S" and Tosoh Corporation under the trademark "TOSFLEX IE-SA48." Further, polymeric systems based on: perfluoro bis-sulfonimides ($CF_3$—[$CF_2SO_2NHSO_2CF_2$]$_n$—$CF_3$); perfluoro phosphonic acids, and the corresponding carbocation acids would function satisfactorily as proton exchange membranes according to the present invention. The Dow experimental PEM gives much superior performance than the "NAFION" PEM materials, which are manufactured by duPont. However, "NAFION" has been determined to be better for impregnating platinum electrodes.

A PEM-impregnated gas diffusion electrode can be hot-pressed onto at least one side of a purified proton exchange membrane, using a Carver hot press, to produce a membrane and electrode (M&E) assembly. The hot-pressing procedure involves placing a sandwich structure, consisting of the PEM and a PEM-impregnated gas diffusion electrode at one or both sides of the PEM, between the platens of the press at approximately 100 psi, where the platens having been previously heated to 100 degrees C. After the temperature of the platens has been raised to within a preselected range of between 125 degrees C. and 230 degrees C., a preselected pressure in the range 1,000 psi to 50,000 psi is applied to the membrane and electrode assembly for a period of time varying from 15 seconds to 150 seconds. The hot pressed M&E's should be immediately removed from the hot press.

Preferred conditions for the preparation of M&E assemblies were found to consist of a hot press temperature of 160 degrees C., a hot pressing time of 90 seconds and a hot press pressure in the range 3,000 psi to 14,000 psi.

Lead dioxide anodes for use in the electrolytic cells of the invention may be prepared by anodic deposition. The choice of anodic substrates on which lead dioxide is deposited are limited since most metals dissolve when deposition is attempted. However, the valve metals, such as titanium, titanium suboxides (such as that produced by Atraverda Limited under the trademark "EBONEX"), platinum, tungsten, tantalum, niobium and hafnium are suitable as substrates for the anodes. When titanium, tungsten, niobium, hafnium or tantalum are utilized as substrate materials, they are first platinized to eliminate passivation problems sometimes encountered with the uncoated substrates. The platinizing process may include a predeposition chemical etch of the substrate material.

Carbon in the form of graphite may be used as a substrate; however, lead dioxide adherence is a particular problem if the carbon has not been thoroughly degassed. The carbon is degassed by boiling in water for some time followed by vacuum drying over a period of days. When degassed, adherence is greatly improved with respect to thermal stress. Vitreous or glassy carbon does not appear to have the adherence problem.

Platinum is the most convenient substrate material to work with, gives the most uniform deposits, and does not present any additional problems. Platinum is therefore typically the most suitable substrate material for lead dioxide anodes. However, its high cost may make other previously mentioned substrate materials more practical for commercial use.

In any event, lead dioxide is plated onto substrates in a well known plating bath comprising essentially lead nitrate, sodium perchlorate, copper nitrate, and a small amount of sodium fluoride and water. The substrate material is set up as the anode in a plating bath with a pH maintained between 2 and 4. Current densities of between 10 and 400 milliamperes per square centimeter give bright, smooth and adherent lead dioxide deposits. Bath temperature is maintained at temperature in the range between 20 degrees C. and 70 degrees C. at all times during deposition. The deposition may be carried out with vigorous stirring of the electrolyte and rapid mechanical vibration of the anode to give consistently fine granular deposits free from pinholes or nodules. A surface active agent may be added to the plating solution to reduce the likelihood of gas bubbles sticking to the anode surface.

A particularly suitable anodic electrode substrate and anodic electrocatalyst for the electrochemical evolution of ozone, using either aqueous electrolytes or solid polymer electrolytes based on cation exchange polymers, is porous titanium coated with a layer of β-lead dioxide. To enhance the adhesion of the β-lead dioxide layer on the porous titanium substrate it has been found that the porous titanium substrate should be suitably cleaned and chemically etched followed by the deposition of a thin layer, or a flash coating, of metallic platinum on the porous titanium substrate immediately prior to the electrodeposition of the β-lead dioxide electrocatalyst layer. However, in experimental work carried out by the inventors, it was found that the nature of the porous titanium substrate has a remarkable effect on the electrochemical ozone generation efficiency and the lifetime of an electrochemical cell for ozone evolution when a solid polymer electrolyte based on a cation exchange polymer membrane, such as perfluorosulfonic acid, is used as the electrolyte.

The Retractable Electrode

The invention provides a means for positioning one or more electrodes into contact with electrolyte and means for retracting the one or more electrodes out of contact with the electrolyte. In a single cell apparatus, it is preferred to have only one mobile electrode, i.e., one positionable and retractable electrode, and one stationary electrode.

The means for positioning and means for retracting may be the same device or different devices. It is preferred that the means for positioning/retracting is designed to retract upon a given shutdown condition, such as a voltage of less than one Volt being applied between the first and second electrodes, expiration of a time period, an ozone concentration greater than a setpoint ozone concentration, contact pressure of less than 5 psig, and combinations thereof. Alternatively, the means for positioning/retracting may be designed to position the one or more electrodes into contact with the electrolyte upon a given production condition, such as a voltage greater than one Volt being applied between the first and second electrodes, expiration of a time period, an ozone concentration less than a setpoint ozone concentration, contact pressure greater than 5 psig, and combinations thereof.

Using a lead dioxide anodic electrocatalyst, it is critically important to prevent the lead dioxide from contacting the acidic environment of the electrolyte while the electrical potential is off. In accordance with the present invention, there are three suitable modes of startup and shutdown. First, the anode must be retracted prior to removing the applied potential, and a suitable potential must be applied prior to contacting the anode to the electrolyte. For example, the voltage may be applied for 30 seconds before the anode initiates contact with the electrolyte and/or applied for 30 seconds following the anode being retracted out of contact with the electrolyte. Second, the voltage may be turned off at the same time as the anode and electrolyte are being separated. Third, the applied electrical potential maybe kept "on", wherein the contacting and retracting of the anode from the electrolyte may act as a switch for turning the current "on" and "off".

In accordance with the invention, it is also useful to provide special startup and shutdown procedures that avoid abrupt changes in the power applied. Accordingly, the procedure may include gradual ramping or incrementally stepping the power between a present value and a target value. Such gradual or incremental increases or decreases in power may be utilized each time the cell is cycled "on" and "off". For instance, the current density through the cell may be stepped several times from 0.15 Amps per square centimeter to eventually arrive at a final current of 3 Amps per square centimeter. Furthermore, a special "initial startup" profile maybe followed during the cell's first use in order to accommodate certain one-time changes in cell conditions from their shipment and storage condition to a fully operational condition, such as the wetting of the membrane that must occur during a first use. In a preferred embodiment, the power may be adjusted so that the cell voltage remains within a given range of voltages most preferably between 3 volts and 8 volts.

While the means for positioning and the means for retracting may be active, passive or a combination of active and passive, it is preferred that the means for retracting is passive and the means for positioning is active. The term "active", as used herein, means that a continuous application of an outside force (electrical, hydraulic, pneumatic, piezoelectric) is necessary to secure the condition or position of the device. For example, an electrical solenoid is an active device because a push rod connected to the solenoid is urged to a desired condition only while electrical power is maintained to the solenoid. The term "passive", as used herein, means that the condition or position of the device will be maintained unless acted upon by an outside force. For example, a wave spring or coil spring is a passive device because a push rod connected to the spring is urged to a desired condition unless the spring is overcome by an opposite outside force. The term "fail-safe", as used herein, refers to the condition or position that a device takes upon a particular failure, such as a loss of electricity.

In a preferred embodiment of the invention, the means for retracting is passive. Passive retraction is accomplished by providing a mechanical stored energy device that maintains a bias on the actuated electrode toward the retracted condition or position, so that retraction occurs automatically upon releasing the actuation force. The mechanical stored energy device may be a spring, a pressurized fluid container, weight, and combinations thereof. In this manner, failure or shutdown of the electrochemical apparatus causes retraction of the electrode.

While positioning and retracting the one or more electrodes are generally directly opposite movements controlled by a guide member, the one or more electrodes may follow any of a number of paths. While the preferred path is a linear path having a guide member that allows only translational movement of the one or more electrodes, it also possible to use an arcuate path having a guide member that allows only hinged movement of the one or more electrodes. Regardless of the exact direction of the path or the type of guide member involved, it is important that the one or more electrodes be positioned to maintain operation of the entire active area of the cell, namely maintain the electrode in fall face contact with the PEM and generally opposite the active area of any opposing electrodes.

The guide member(s) may be provided in various forms, including those that guide the push rod and those that guide the electrode itself. Furthermore, the guides may be disposed through or around the electrode or push rod, or consist only of a rigid connection with the positioning means. In addition to providing alignment of the electrodes and PEM, it is preferred that the guide member limit rotational and lateral movement of the electrode relative to the face of the PEM. Rotational and lateral movement are undesirable not only because of potential physical damage to the PEM or electrocatalyst, but also because consistent realignment of the electrocatalyst and PEM from one operating cycle to the next allow any physical variation in the electrocatalyst and PEM surfaces to conform to each other as they do in a traditional cell where the electrocatalyst and PEM are in constant compression. Consistent re-alignment of the electrocatalyst coated substrate and PEM from one operating cycle to the next is preferred in accordance with the present invention.

The electrolyte used in the electrochemical apparatus of the present invention may be either a liquid electrolyte or a solid electrolyte (otherwise referred to as an ion exchange membrane), such as a PEM. Ion exchange membranes are preferred, because liquid electrolytes must be maintained separate from the process water. While an electrochemical cell will function with the electrodes merely contacting the membrane, it is preferred to support the membrane on one of the electrodes. This support may include securing the membrane to be stationary with respect to one of the electrodes or directly bonding or casting the membrane onto one of the electrodes. An example of a suitable bonding procedure includes heating a perfluorinated sulfonic acid polymer membrane to about 160° C. under a pressure of up to 300 psi, preferably for about 90 seconds. When using a lead dioxide anodic electrocatalyst, the ion exchange membrane is secured to the cathode.

The cathode may be open to the air and have no direct supply of water. Such a cathode may be suitable for air depolarization as well as evaporative disposal of both the electroosmotic water and any product water. However, since the membrane must be kept wet or moist in order to be ionically conducting, a source of water must be provided to the membrane. Optionally, water may be provided from the anode side, either as liquid water or water vapor. Further, water may be provided from the cathode side for back diffusion into the membrane, either as liquid water (no air depolarization) or water vapor. Even further, water may be provided to an edge or other exposed area of the membrane so as to "wick" or absorb water into the membrane. Particularly in applications where water of sufficient quality is scarce, it is anticipated that the hydration state of the membrane may be controlled or limited to make more efficient use of water while accepting a reduction in the ionic conductivity of the membrane. Where the amount of water being supplied to the membrane is limited, electroosmotic water and product water at the cathode will be absorbed (back diffused) into the membrane.

While much of the description and drawings of the present invention refer to a single cell, the invention encompasses multiple cell arrangements, including both stacks of cells and side-by-side arrays of cells. It should be recognized that both stacks and side-by-side arrays can be electronically coupled in either a parallel or series circuit depending upon the arrangement of electronic conductors and insulators. However, the configuration of a plurality of cells in a side-by-side array may include a plurality of cells in the same plane, a plurality of cells in two or more parallel planes, and a plurality of cells along a curvilinear surface. The commonly owned U.S. patent application Ser. No. 09/598,067 is incorporated by reference herein.

The electrolytic cells may generate gas at any concentration, but the gas concentration preferably comprises between about 1% and about 18% by weight ozone in oxygen. Such electrolytic cells are described in U.S. Pat. No. 5,460,705 which description is incorporated by reference herein. A fully passive electrolytic cell for producing ozone is most preferred for small scale point-of-use applications such as point-of-use water treatment or built into equipment requiring ozone for sterilizing, disinfecting, decontaminating, washing, etc. The limited number of moving parts reduces the initial cost of the device and also reduces the potential for failure and maintenance requirements of the device.

In the description of the Figures that follow, like numerals may be used to refer to like elements among the Figures. The use of like numerals for like elements means that the like elements have the same general name and function, but like elements may have more or fewer features in one Figure than the same element in another Figure. The use of like numerals is intended to more clearly describe the common elements of the embodiments as they appear from Figure to Figure, and a particular use of like numerals should not be taken as limiting the scope of the invention to specific features unless the description expressly states such limitations.

Figures 2, 3:
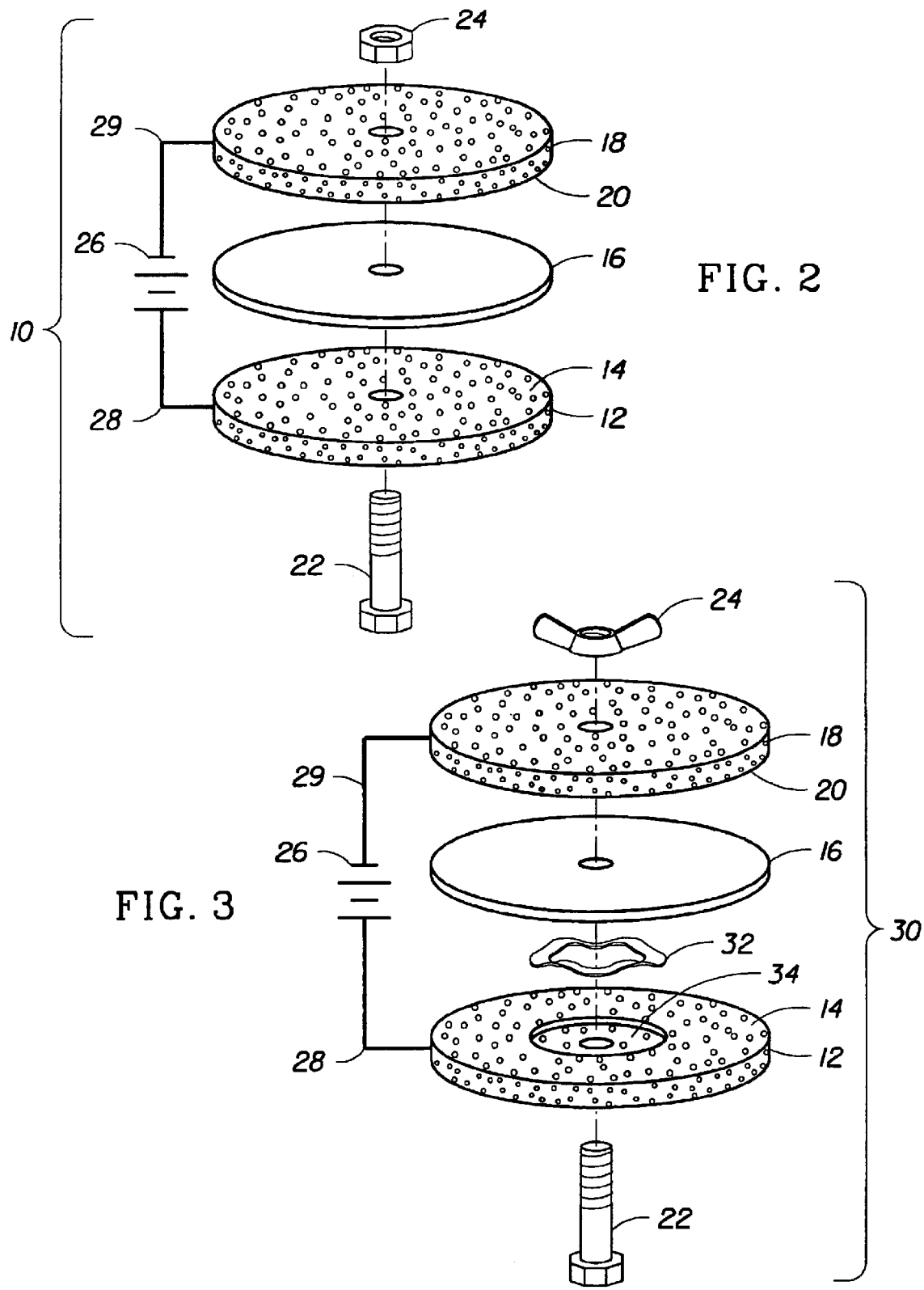
FIG. 2 is a single electrochemical cell capable of positioning electrodes into compressed contact with an ion exchange membrane.
FIG. 3 is an alternative single electrochemical cell having a wave spring to retract an electrode away from the ion exchange membrane when there is no compression.

FIG. 2 is an exploded view of a single electrochemical cell 10 capable of positioning two electrodes into compressed contact with an ion exchange membrane. The cell 10 comprises an electronically conducting anode substrate 12 having an anodic electrocatalyst 14 formed on the surface facing the PEM 16. However, the anode substrate may also function as both substrate and electrocatalyst. An electronically conducting cathode substrate 18 has a cathodic electrocatalyst 20 formed on the surface facing the PEM 16. However, the cathode substrate may also function as both substrate and electrocatalyst. The anode substrate 12, cathode substrate 18 and PEM 16 are secured together by an electrically nonconducting bolt 22 and nut 24. A power supply 26 has a positive terminal 28 and a negative terminal 29 placed in electronic communication with the anode substrate 12 and cathode substrate 18 via electronic conductors, respectively. The power supply applies the necessary electrical potential (Volts) to drive the electrochemical process. In one embodiment of the invention, the cell 10 is submersed in water so that water is provided to and electrolyzed at the anodic electrocatalyst to form a mixture of ozone/oxygen gas and water is provided directly or indirectly to the PEM to support proton conductivity. Hydrogen gas or other cathodic product(s) is formed at the cathodic electrocatalyst.

The anode and cathode substrates are electronically conducting metal or ceramic particles or fibers that yield a porous substrate usually in the form of a disc, square or rectangle. Exemplary substrates include, but are not limited to, woven felt, sintered metal, metal screens, metal meshes, fabrics and the like.

FIG. 3 is an exploded view of an alternative single electrochemical cell 30 having a separation spring 32, such as a wave spring or wavy washer, to retract the anode substrate/electrocatalyst 12, 14 away from the ion exchange membrane 16 when the compression is relaxed, such as when the nut 24 is threaded away from the head of the bolt 22. The anode substrate 12 preferably has a recess 34 to receive the compressed wave spring during operation and to maintain alignment (centering) of the wave spring with the anode substrate 12 so that the substrate 12 will be pushed away from contact with the PEM 16. In applications where it is important to minimize the retraction distance, it is beneficial to retract the substrate 12 an equal distance at all points over the substrate surface, such as with a substantially translational movement.

While the retraction or separation distance may be any distance at which the one or more electrodes are moved out of contact with the PEM, a controlled translational retraction can allow very small retraction distances dependent upon the dimensional tolerances of the actuator and guide member, typically on the order of 1–5 millimeters, but certainly retractions of more than 5 millimeters and less than 1 millimeter are possible. While the present invention does not reside in any particular separation distance, reference to a separation of "up to" a certain distance must avoid contact between the separated components, but may be as close as possible given dimensional tolerances of the relevant parts.

The term "retraction", as used herein, means movement that causes separation of components. The term "actuation", as use herein, means movement that causes contact between components. Neither "retraction" nor "actuation" should be taken to imply whether a pushing or pulling force is used to accomplish the separating or contacting movement unless such pushing or pulling is expressly stated. In general, where the Figures show retraction accomplished by a pushing force, it should be recognized that a pulling force could be easily adapted to accomplish the same movement. However, where springs are involved, as shown in numerous Figures herein, it is preferred, but not required, that the springs be placed in compression rather than tension.

Figure 4A:
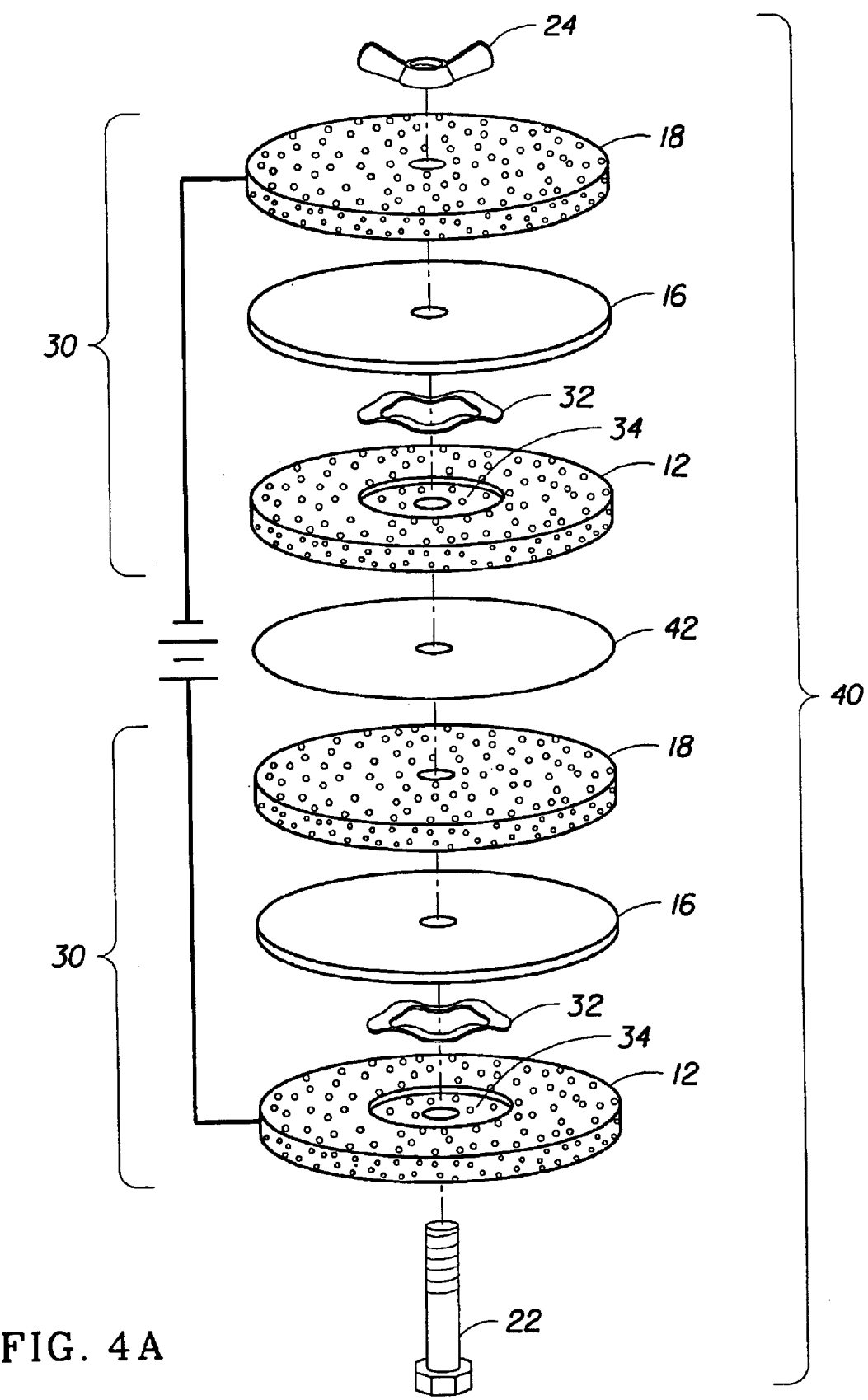
FIG. 4A is an electrochemical cell stack having a bipolar plate between two cells of FIG. 3.

FIG. 4A is an exploded view of an electrochemical cell stack 40 having a bipolar plate 42 disposed between two cells, such as a pair of cells 30 from FIG. 3. In the manner shown, even a stack of cells can include a passive retraction mechanism (for example, one wave spring 32 per cell) and an active actuation mechanism (for example, a bolt 22/nut 24 combination). As shown in FIGS. 2–4, the bolt 22 also serves the function of a guide member that maintains alignment of the components.

Figure 4B:
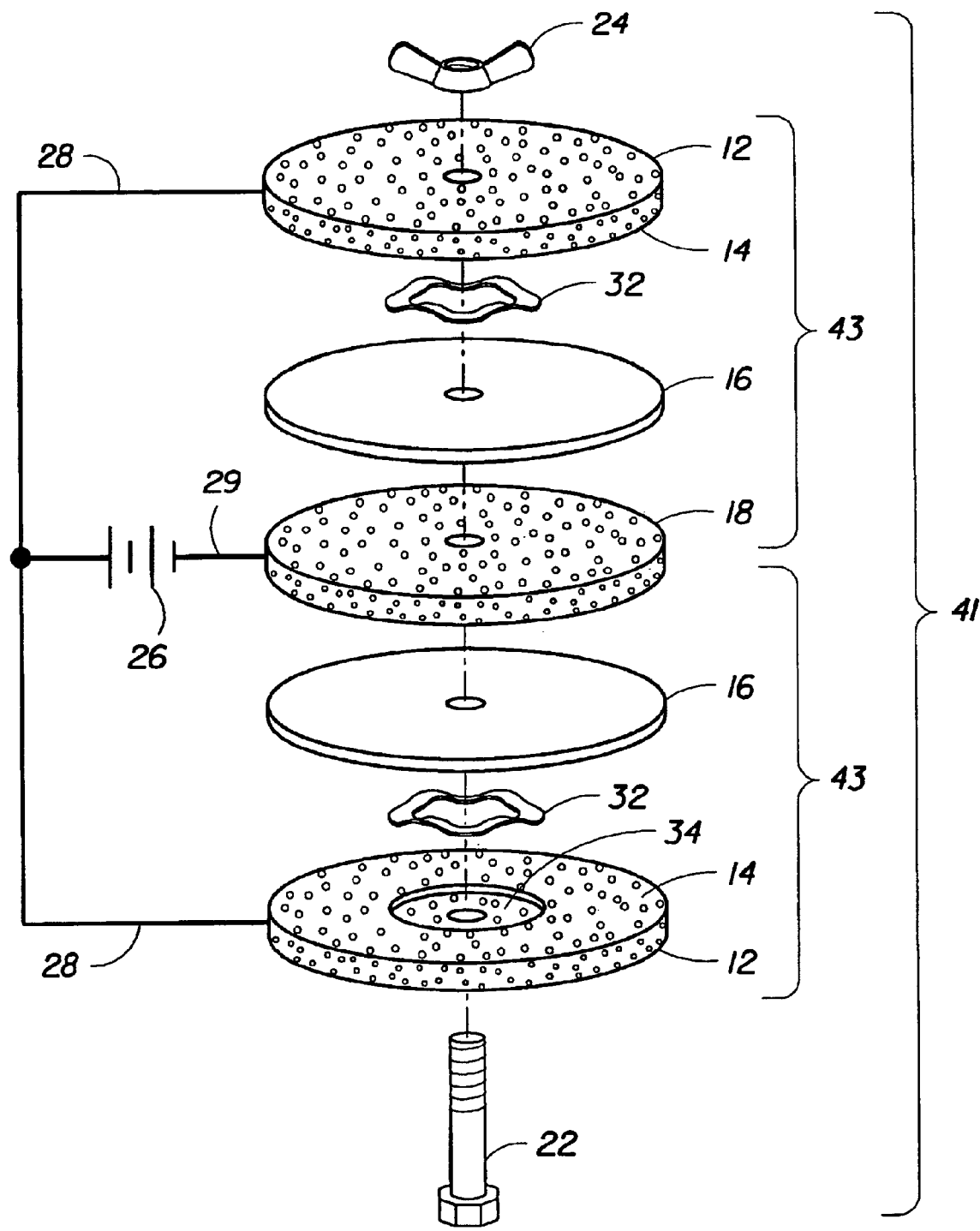
FIG. 4B is an electrochemical cell stack having two cells with a common cathode.

FIG. 4B is an electrochemical cell stack 41 having two cells 43 with a common cathode substrate 18 coupled to the negative terminal of a power source. The two cells 43 are mirror images, but in other respects the stack 41 is the same as the stack 40 of FIG. 4A. It is also possible to operate a cell having a common anode and two cathodes.

Figure 5A:
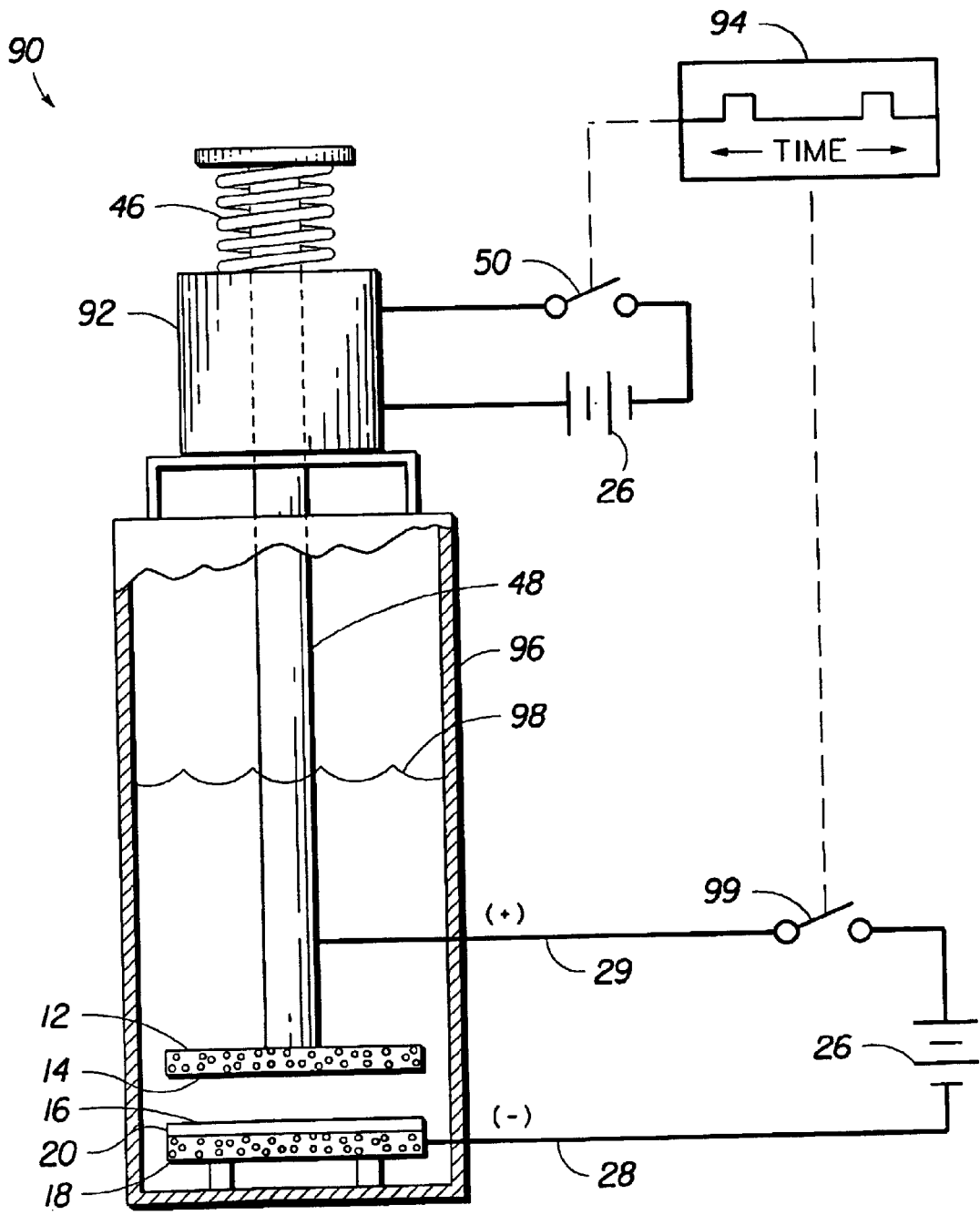
FIG. 5A is a schematic side view of an electrochemical cell having an anode coupled to a push rod, wherein an electrical solenoid actuator with a return spring controls the positioning of the push rod.

FIG. 5A is a schematic side view of an electrochemical apparatus 90 having an anode substrate 12/electrocatalyst 14 coupled to a push rod 48, wherein the positioning of the push rod is controlled by an electrical solenoid actuator 92 to compress the anode substrate 12/electrocatalyst 14 against the PEM 16 and a return spring 46 to retract the anode. The cathode substrate 18/cathodic electrocatalyst 20/PEM 16 assembly as well as the solenoid actuator 92 are secured in a fixed relationship, such as by securing to a common housing 96, so that movement of the anode is achieved relative to the cathode/PEM simply by activating the actuator. The cell is shown submersed in water 98 while the solenoid 92 is positioned out of the water. As used in the examples below, a controller 94 is connected in the electronic circuit to provide power to the solenoid 92. The controller 94 may operate the apparatus 90 in any number of ways based on a variety of conditions, such as a simple timer specifying the "on" duration and frequency.

Figure 5B:
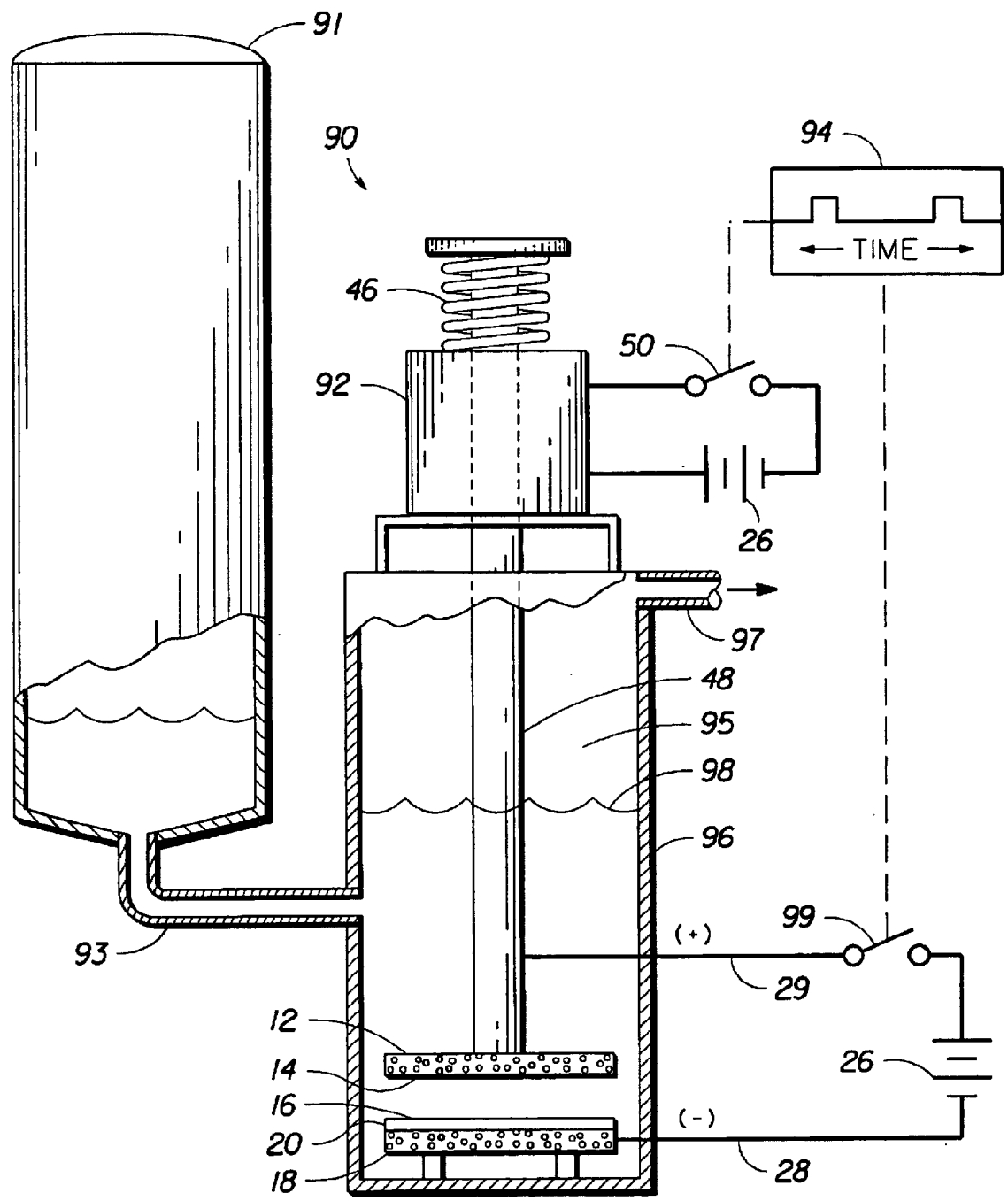
FIG. 5B is a schematic side view of the electrochemical cell of FIG. 5A having a separate deionized water reservoir.
Figure 7A:
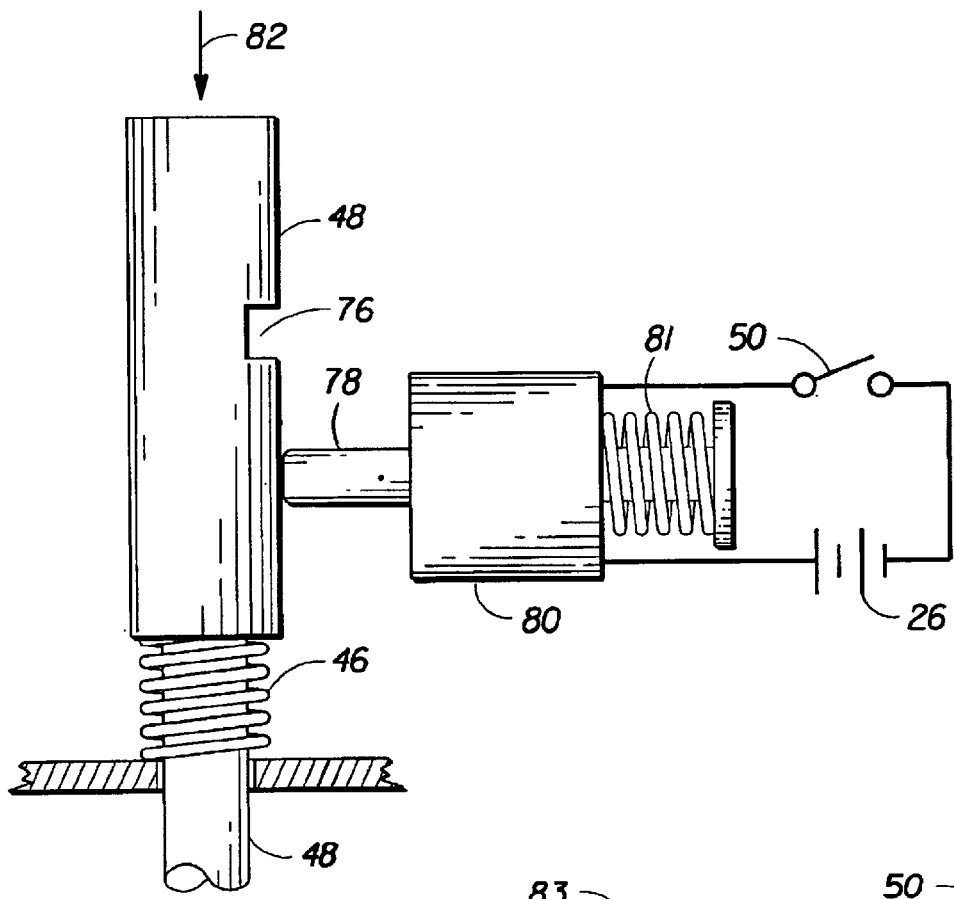
FIGS. 7A–B illustrate exemplary means for latching a push rod to secure an electrode in contact with the PEM during the application of electricity.

FIG. 5B is a schematic side view of the electrochemical apparatus 90 of FIG. 7A having a separate deionized water reservoir 91 that is preferably prepackaged deionized water. The water reservoir 91 is provided in fluid communication with the housing 96 through a conduit 93. The water reservoir 91 preferably contains deionized water to provide high quality water to the apparatus and to eliminate the need to incorporate filtration and deionization devices into the apparatus. The water level in the reservoir 91 is controlled within certain limits, since the reservoir 91 will add water to the housing 96 whenever the water level in the housing 96 falls below the level of the inlet conduit 93 to allow a gas bubble to pass into the housing 91. The headspace 95 above the water level allows phase separation of the ozone/oxygen gas from the water 98 so that the ozone/oxygen gas can then pass through the ozone output 97, preferably having a valve (not shown) to regulate the withdrawal of gas and/or maintain a backpressure.

Figure 5C:
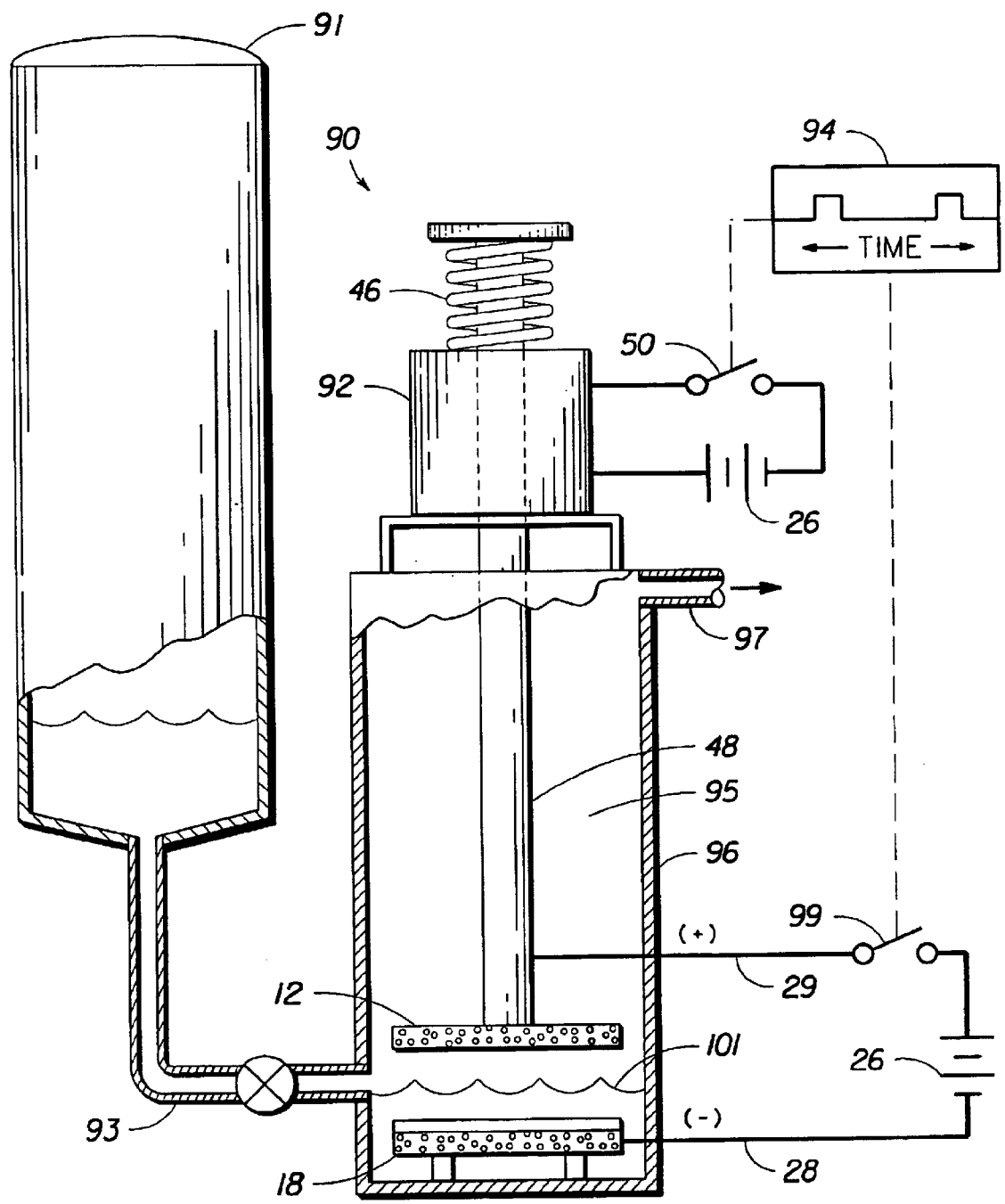
FIG. 5C is a schematic side view of the electrochemical cell of FIG. 5B arranged to withdraw the electrode out of contact with a liquid electrolyte.

FIG. 5C is a schematic side view of the electrochemical apparatus 90 of FIG. 5B arranged to withdraw the electrode 12 out of contact with a liquid electrolyte 101. The apparatus is the same as in FIG. 5B except that the ion exchange membrane 16 has been replaced by a liquid electrolyte 101 and that the conduit 93 communicates with the housing 96 to maintain the electrolyte level over the cathode 18, yet low enough that the anode 12 can be retracted out of contact with the electrolyte.

Figure 6A:
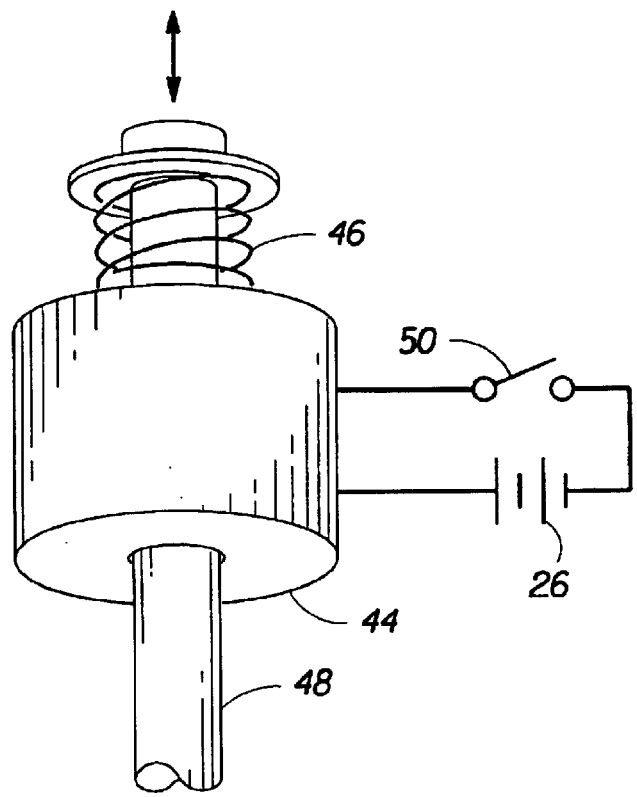
FIGS. 6A–F illustrate exemplary means capable of actuating or positioning an electrode to make contact with an electrolyte, the means including an electrical solenoid with spring retraction (6A), a cam with spring retraction (6B), a hydraulic or pneumatic actuator (6C), a lead screw (6D), rack and pinion (6E), and piezo-electric actuator (6F), respectively.
Figure 6B:
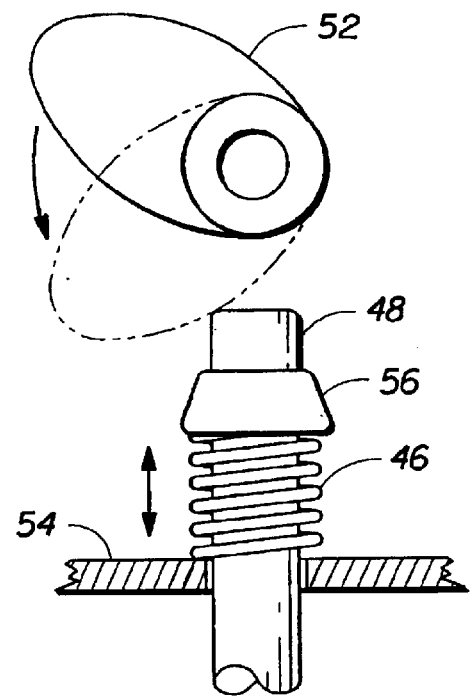
Figure 6C:
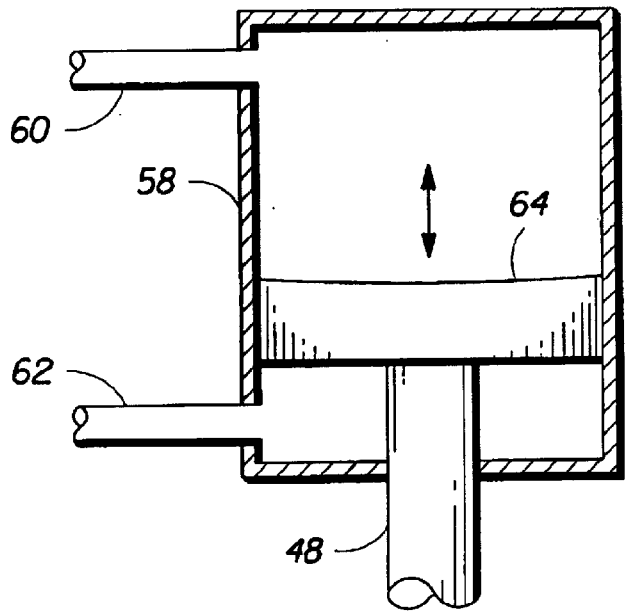
Figure 6D:
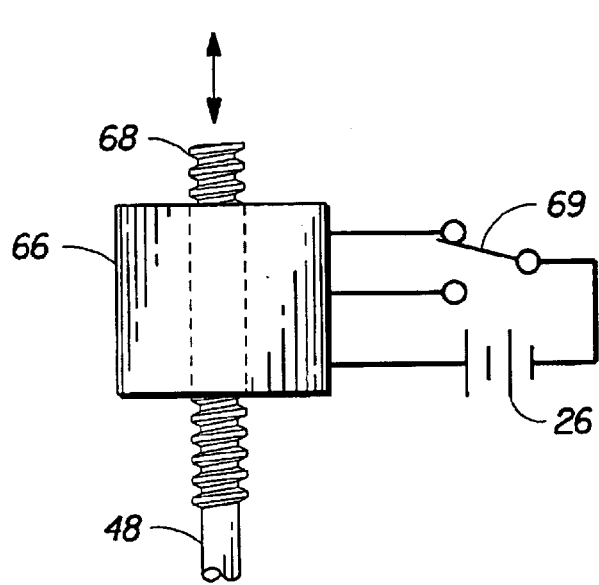
Figure 6E:
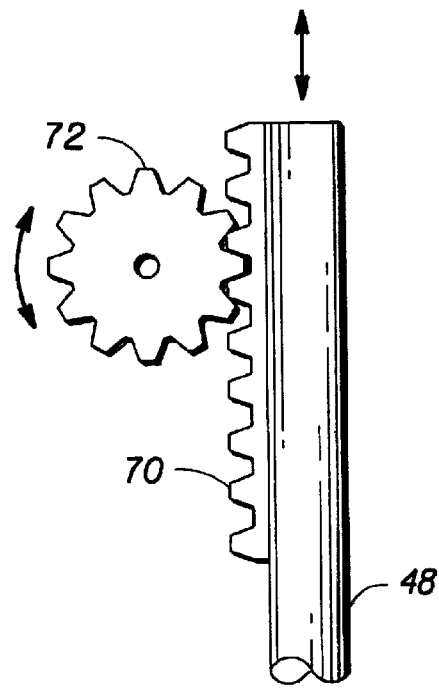
Figure 6F:
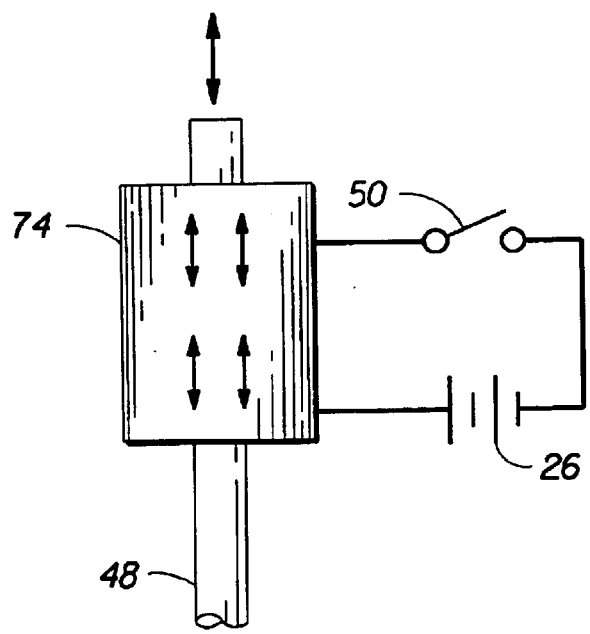

FIGS. 6A–F illustrate exemplary means capable of actuating or positioning an electrode to make contact with electrolyte, the means for positioning including: an electrical solenoid 44 for actuating the push rod 48 upon throwing a switch or receiving a command from a controller 50 in combination with a spring 46 for passively retracting the push rod (FIG. 6A); a cam 52 aligned to actuate the push rod 48 having a spring 46 disposed between a retainer 54 and a collar 56 for providing passive retraction of the push rod (FIG. 6B); a hydraulic or pneumatic actuator 58 has a push rod 48 coupled to a piston 64, where the actuator 58 includes a motive fluid feed conduit 60 for actuating and a motive fluid return conduit 62 for retracting the piston 64/push rod 48 (FIG. 6C); a lead screw 68 push rod 48 and a lead screw motor 66 connected to power source 26 through manual switches or an electronic controller 69 (FIG. 6D); a rack 70/push rod 48 and pinion 72 (FIG. 6E, motor/power source not shown); and a piezo-electric actuator 74 coupled to the push rod 48 and activated by power source 26 through switch 50 (FIG. 6F). Other actuating or positioning devices and variations of the foregoing devices are deemed to be within the scope of the present invention.

Figure 7B:
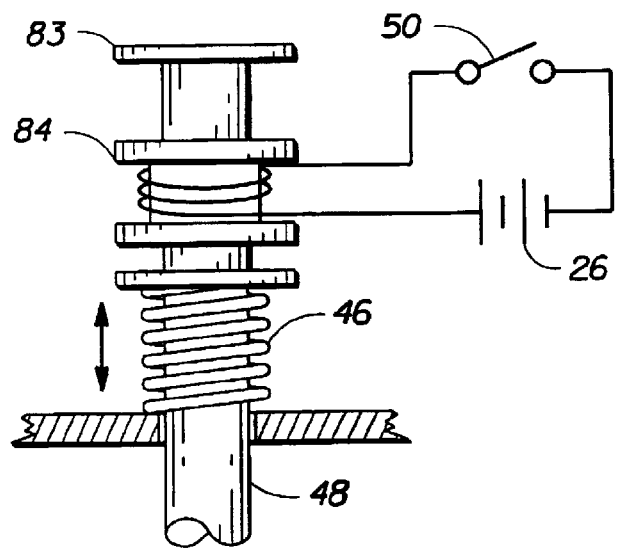

FIGS. 7A–B are schematic diagrams of exemplary devices for latching the push rod 48 in a position that secures an electrode (not shown) in contact with the PEM during the application of electricity. In FIG. 7A, the push rod 48 includes a latching notch 76 designed to receive an extendable shaft 78 of a latching solenoid 80 upon application of electricity. In the absence of electrical power or upon the occurrence of some other standby event, such as low cell voltage, the solenoid relaxes and the return spring 81 withdraws the shaft from the notch. If there is no longer an actuating force 82 being applied, then the spring 46 causes retraction of the push rod. In FIG. 7B, the push rod 48 is coupled to an electromagnetic armature 83 that can be selectively secured to an electromagnet coil latch 84 coupled to a power source 26 through a switch 50. Upon releasing the electromagnetic latch 84, the spring 46 causes retraction of the push rod.

In FIGS. 6A–F and 7A–B it should be appreciated that in order to accomplish movement of the push rod, the elements causing or preventing movement of the push should be secured to the housing or other stationary structure of the electrochemical apparatus.

Figure 8:
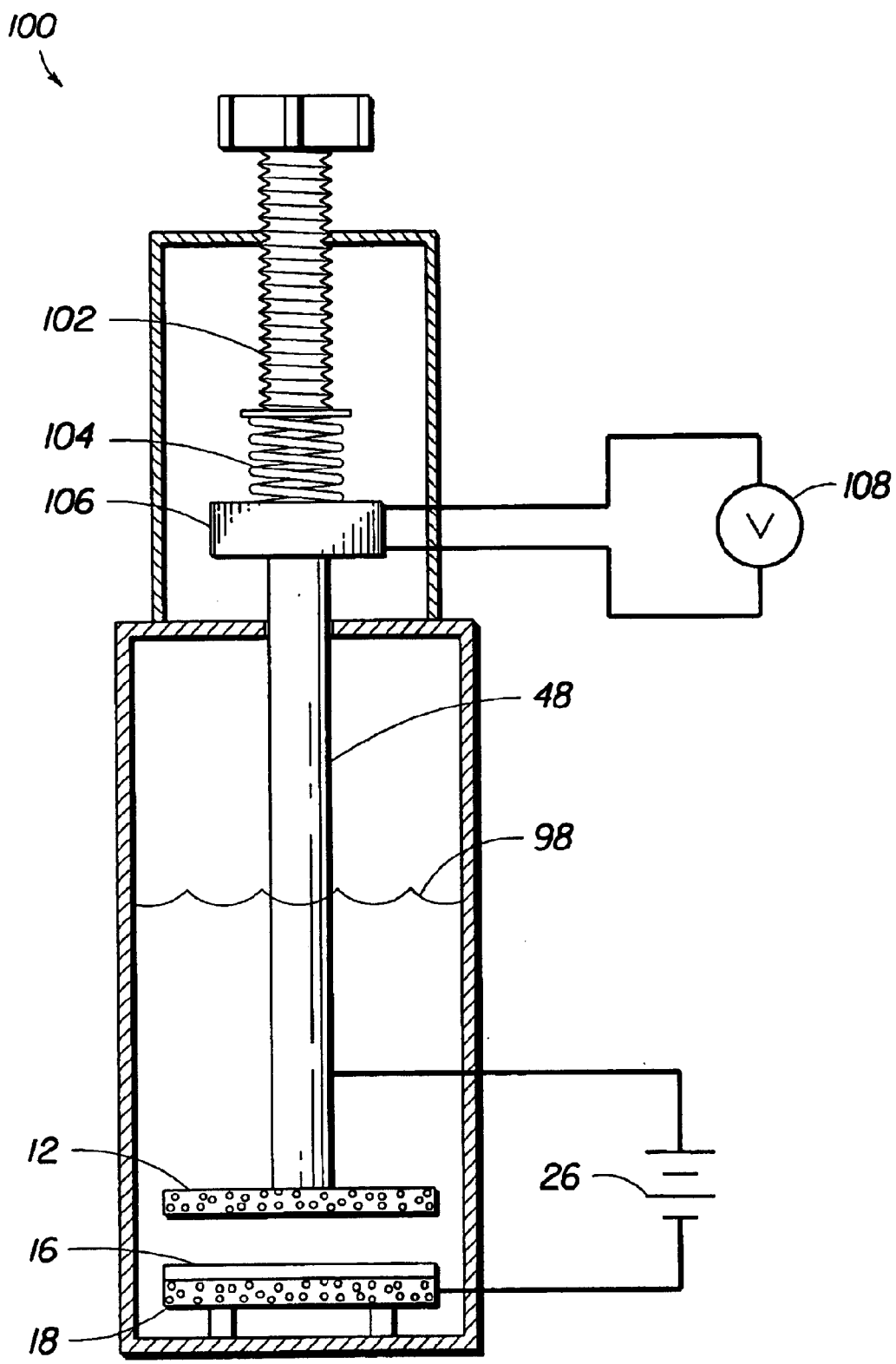
FIG. 8 is a schematic side view of an experimental electrochemical cell setup having an adjustable load and load cell for monitoring the cell operation as a function of compression force between the electrode and the PEM.

FIG. 8 is a schematic side view of an experimental electrochemical cell setup 100 having an adjustable load, such as a bolt 102 and spring 104, and a load cell 106 for measuring the load and displaying or recording the load with a meter 108. The ozone production efficiency can be monitored as a function of compression force between the electrode and the PEM. It is the compression force per unit area that is believed to be important to optimal cell performance.

Figure 9:
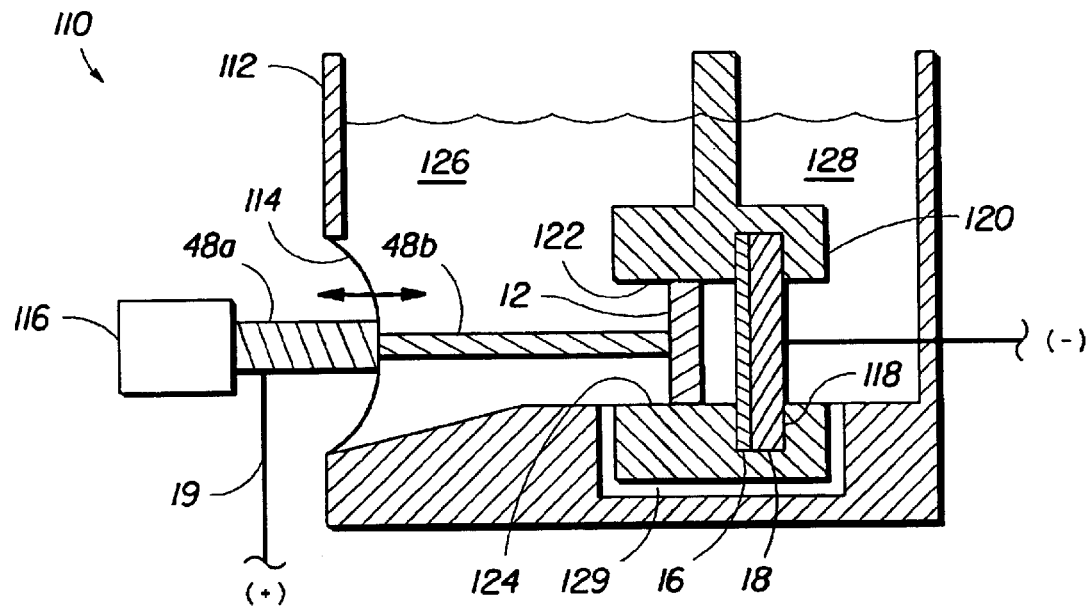
FIG. 9 is a schematic side view of an electrochemical apparatus having a water reservoir and a diaphragm allowing sealed movement of the push rod.

FIG. 9 is a schematic side view of an electrochemical apparatus 110 having a water reservoir or housing 112 and a sealing member, such as diaphragm 114, allowing fluid-sealed movement of the push rod end 48a coupled to the positioning member 116 that is isolated from the water and the push rod end 48b coupled to the anode 12. Optionally, the sealing member may be piston rings, shaft seals and the like.

As shown, the cathode 18 and PEM 16 are stationarily secured at the top and bottom to floor 118 and interior wall 120 portions of the housing 112. The anode 12 is maintained in alignment with the cathode/PEM by a guide member comprising the surfaces 122, 124, which are preferably circumferential about the anode 12. The apparatus 110 is also shown having an anode chamber 126 isolated from a cathode chamber 128. One benefit of the isolation is the separation of the anode gas(es) from the cathode gas(es). However, as a consequence of the isolation and the electroosmotic flow of water from the anode to the cathode, it is beneficial to have a conduit 129 in the apparatus 110 to allow the return of water from the cathode chamber 128 to the anode chamber 126 without mixing the gas(es).

Optionally, the invention provides a unique gas destruct system which can destruct waste hydrogen and/or ozone. The hydrogen is mixed with oxygen (or air) and passed over a hydrogen destruction catalyst producing heat. The hot gases, including excess oxygen may then be combined with waste ozone and passed downstream over an ozone destruction catalyst. Since the ozone generator continuously produces hydrogen, the heat from the hydrogen destruction maintains the ozone catalyst at elevated temperatures to make the catalyst more active and to continuously dry the ozone destruct. In this manner, the ozone destruct catalyst is maintained in a ready state for the destruction of ozone. Alternatively, the hydrogen destruct can provide high-grade heat that may be used in other, unrelated processes, such as domestic hot water heating. U.S. Pat. No. 5,989,407 and U.S. patent application Ser. No. 09/383,548 filed on Aug. 26, 1999 are incorporated by reference herein.

Figure 10A:
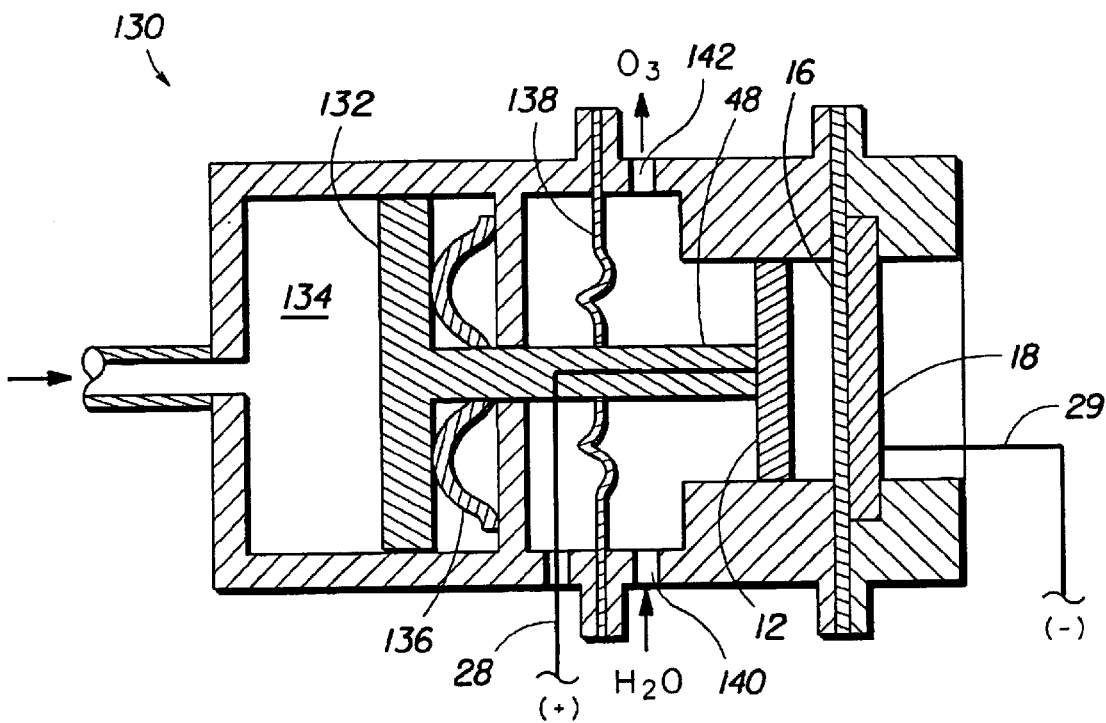
FIG. 10A is a schematic side view of an alternative electrochemical apparatus having a hydraulically actuated anode.

FIG. 10A is a schematic side view of an alternative electrochemical apparatus 130 having a hydraulically actuated anode, wherein the motive fluid may be the process water or another fluid. The anode 12 is coupled to the push rod 48 that has a piston 132 on the opposing end. The piston 132 is actuated by a fluid entering the piston headspace 134 to compress the return spring 136 and position the anode into compressed contact with the PEM 16. The apparatus has an optional diaphragm 138 attached around the push rod 48 to maintain isolation of the process water, which enters through the passage 140 and exits with gases produced through passage 142, from the motive fluid.

The cathode 18 is stationary with the PEM 16 secured to the cathode. Notably, there is no cathode chamber or reservoir around the cathode, but rather the cathode is open to the air and maybe referred to as "dry". The open or exposed cathode may be suitable for air depolarization as well as evaporative disposal of both the electroosmotic water and any product water. Accordingly, there is no direct supply of water to the cathode.

Figure 10B:
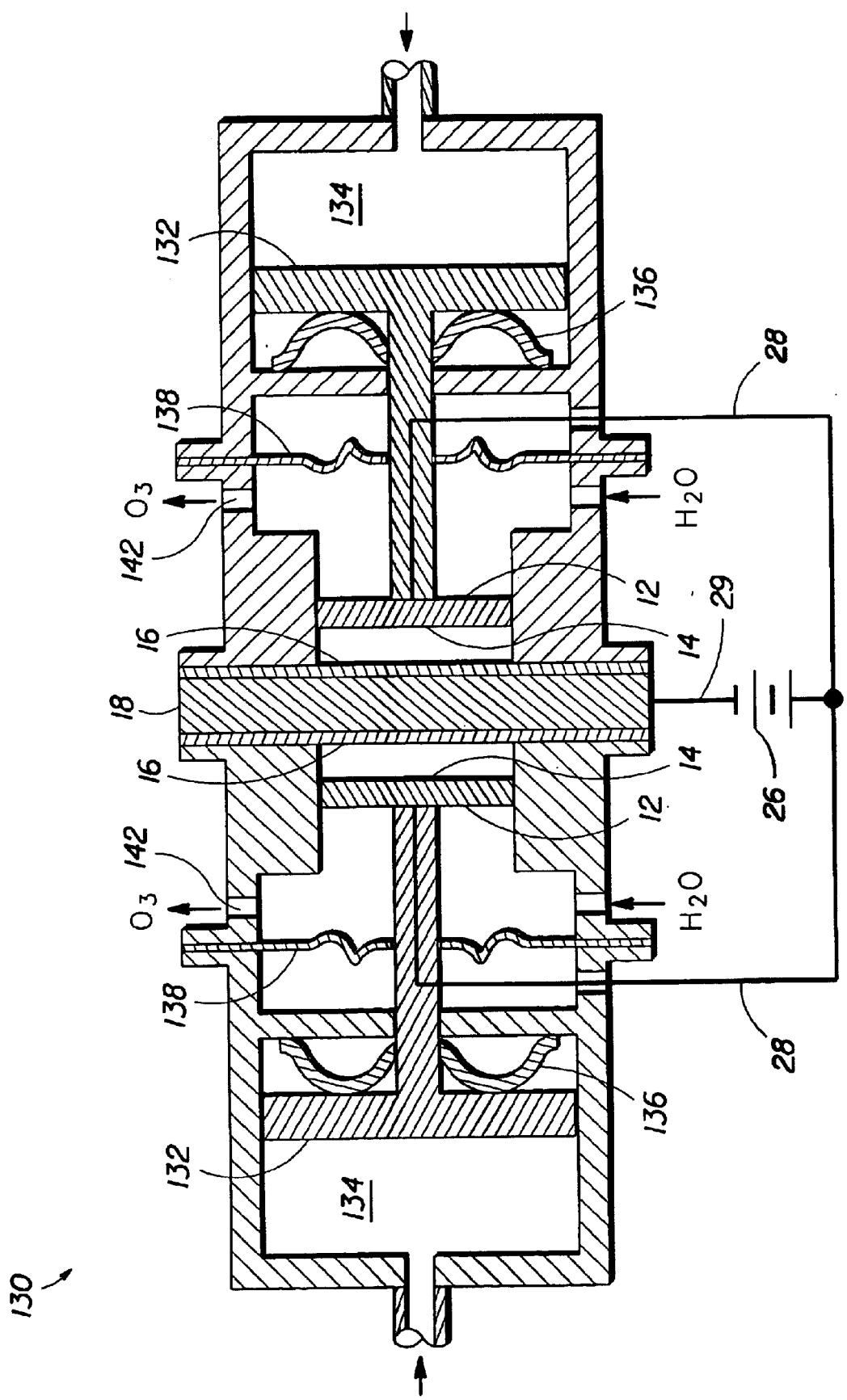
FIG. 10B is a schematic side view of two electrochemical cells/apparatus according to FIG. 10A, but having a common cathode therebetween.

FIG. 10B is a schematic side view of two electrochemical cells/apparatus according to FIG. 10A, but having a common cathode therebetween. The common cathode 18 is coupled to a power source 26 as in FIG. 4B. However, the apparatus of FIG. 10B has two mobile anodes 12 coupled to two means for positioning and retracting, which operate the same as the individual means of FIG. 10A. The two means may be actuated by the same or different motive fluids and may be actuated and retracted at the same or different moments. It is anticipated that the two mobile electrodes may vary from each other in any of a number of characteristics, for example catalyst loading, amount of active area, and types or concentrations of products produced. Optionally, the two electrodes may be operated independently to produce solutions that are optimized for different uses, such as using one anode for producing an 18 weight percent ozone solution for sanitizing countertops and using another anode for producing 2 weight percent ozone to cleanse skin burns.

Figure 11:
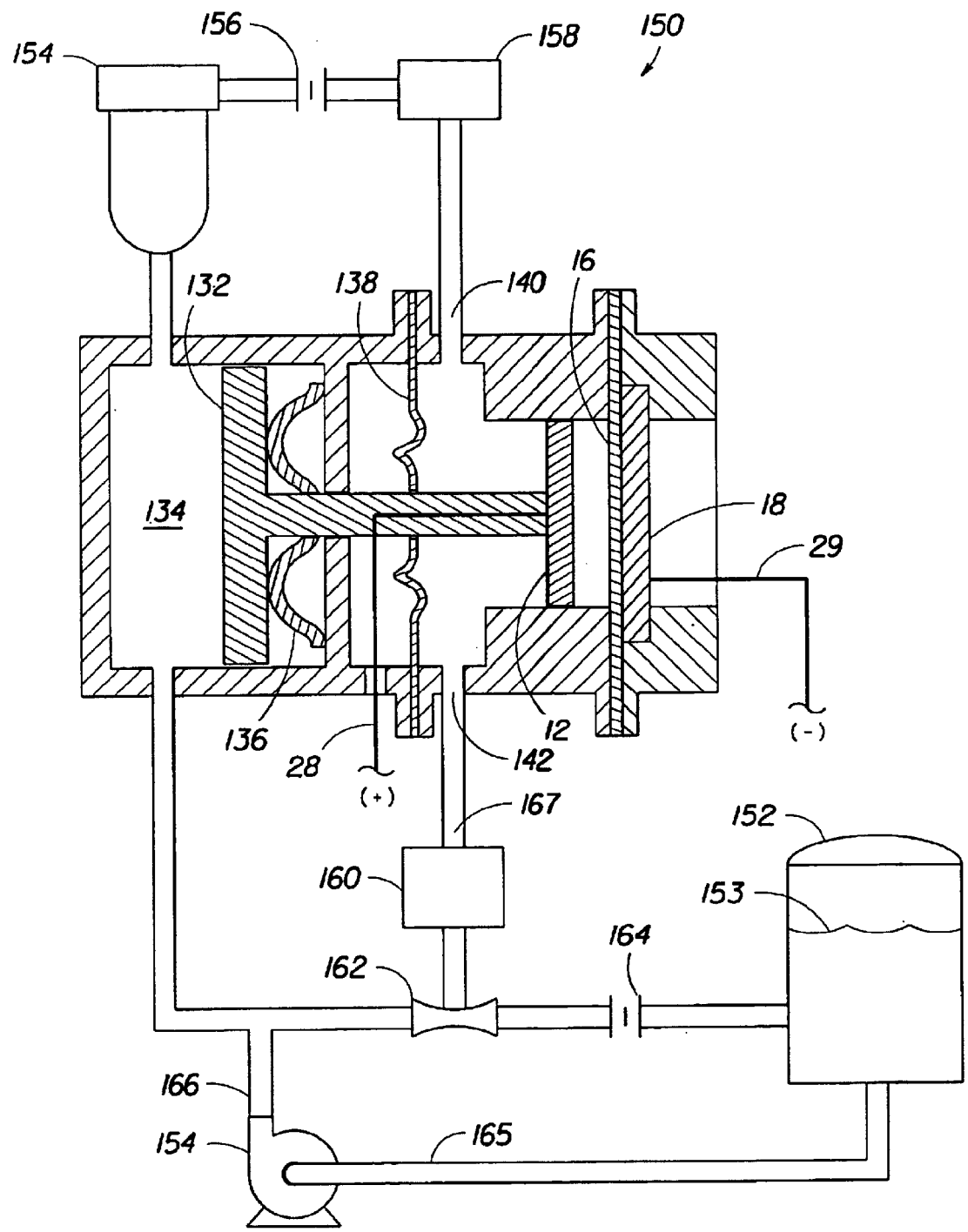
FIG. 11 is a schematic side view of an alternative electrochemical apparatus having a process water reservoir and a pump that delivers process water to the electrochemical cell as well as to an integral hydraulic actuator.

FIG. 11 is a schematic side view of an alternative electrochemical apparatus 150 having a process water reservoir 152 and a pump 154 that delivers process water 153 to the electrochemical cell (anode substrate 12, PEM 16, cathode substrate 18) as well as to an integral hydraulic actuator. The hydraulic actuator is similar to that of FIG. 10, except that the piston 132 is actuated with the process water 153. The apparatus is also provided with a filter 154, preferably a carbon filter, to remove, among other things, particulates, dissolved organic compounds and heavy metals (also acting as an ozone destruct catalyst), a flow controller 156 (such as a flow restricting orifice), a deionization resin bed 158 to remove dissolved ions from the process water 153, a lead removing unit 160 (such as a column of zeolite, alumina, silica or other materials known to bind or adsorb lead ions and particulate or colloidal lead species), a venturi 162, and a backpressure control orifice 164. It should be recognized that the order of the filter 154, flow controller 156 and deionization resin bed 158 is not restricted.

In operation, water 153 from the reservoir 152 is provided to the inlet of pump 154 through a reservoir discharge conduit 165. The pump discharge conduit 166 provides high-pressure water for delivery to the piston motive fluid chamber 134 or through the venturi 162 and backpressure control orifice 164 back to the reservoir 152. The high pressure process water actuates the piston as in FIG. 10, but then the process water passes through the carbon filter, flow controller and deionization resin bed on its way to the anode chamber. The deionized water supports electrolysis at the anode 12 as well as proton conductivity through the PEM 16 to the cathode 18. The electroosmotic water passing to the cathode 18 may be recycled or discarded (i.e., dumped into a drain or allowed to evaporate). However, the water that is not used in the anode becomes ozonated and the water escapes the anode chamber along with the ozone/oxygen gas stream through discharge conduit 167 and passes through the lead removal unit 160. Downstream of the lead removal unit 160 the ozonated water and the ozone/oxygen gas stream are drawn into the venturi and returned to the reservoir 152 where the concentration of ozone is allowed to increase.

The startup of an electrochemical apparatus, such as the apparatus 150 of FIG. 11, may proceed in many ways, but it is preferred that the startup include: (1) introducing process water into the water reservoir, (2) applying a voltage between the first and second electrodes, (3) turning on the water pump, and (4) positioning the mobile electrode into contact with the electrolyte, most preferably in the order stated.

Figure 12:
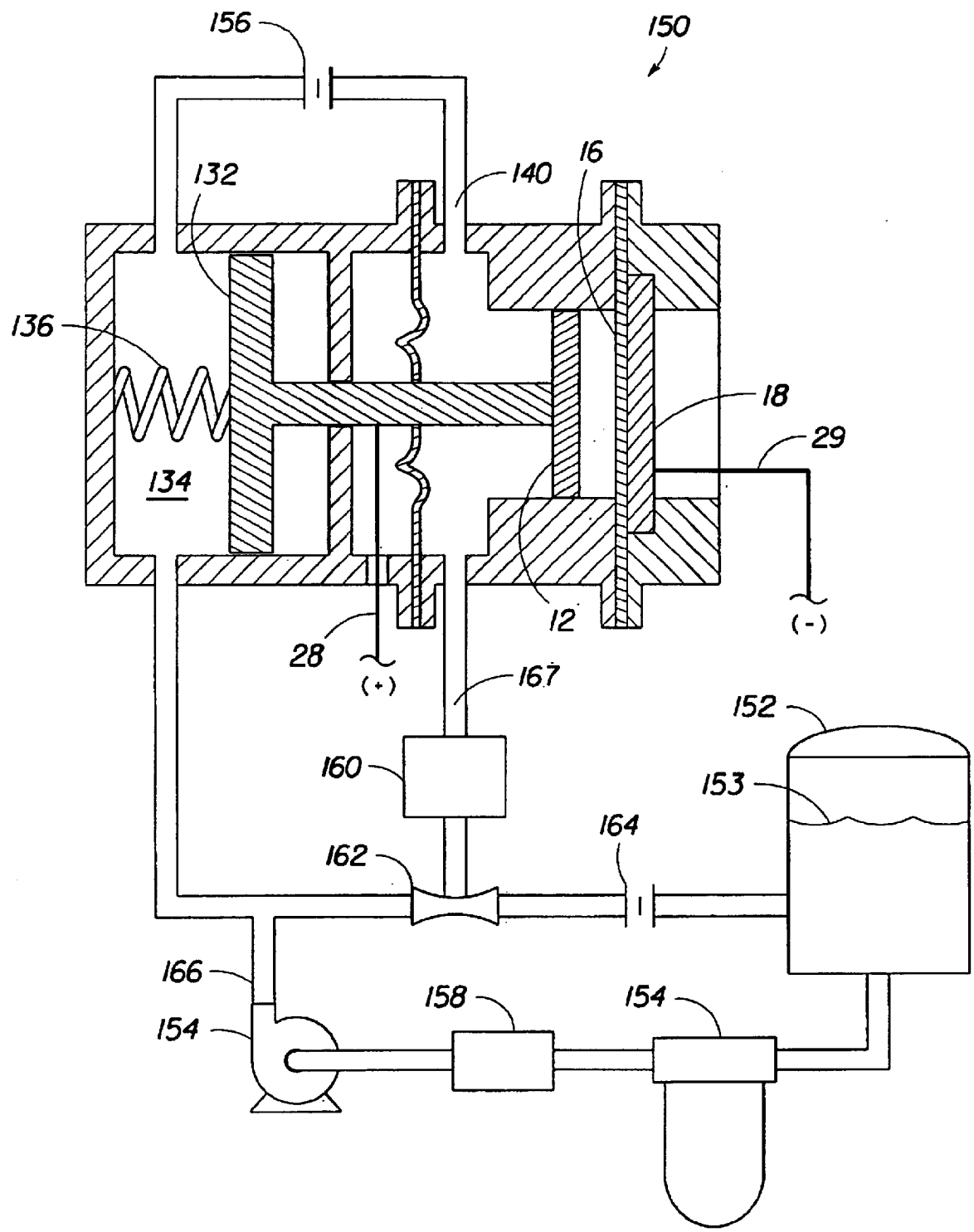
FIG. 12 is a schematic side view of the electrochemical apparatus of FIG. 11 having the carbon filter and deionization bed relocated to the pump inlet.

FIG. 12 is a schematic side view of the electrochemical apparatus 150 of FIG. 11 having the carbon filter 154 and deionization bed 158 relocated to the reservoir discharge conduit 165. Also, the flow control orifice 156 is left between the motive fluid chamber 134 and the anode chamber in order to maintain or enhance the pressure differential acting upon the piston 132. It is also shown that the return spring 136 can be disposed in tension.

Figure 13A:
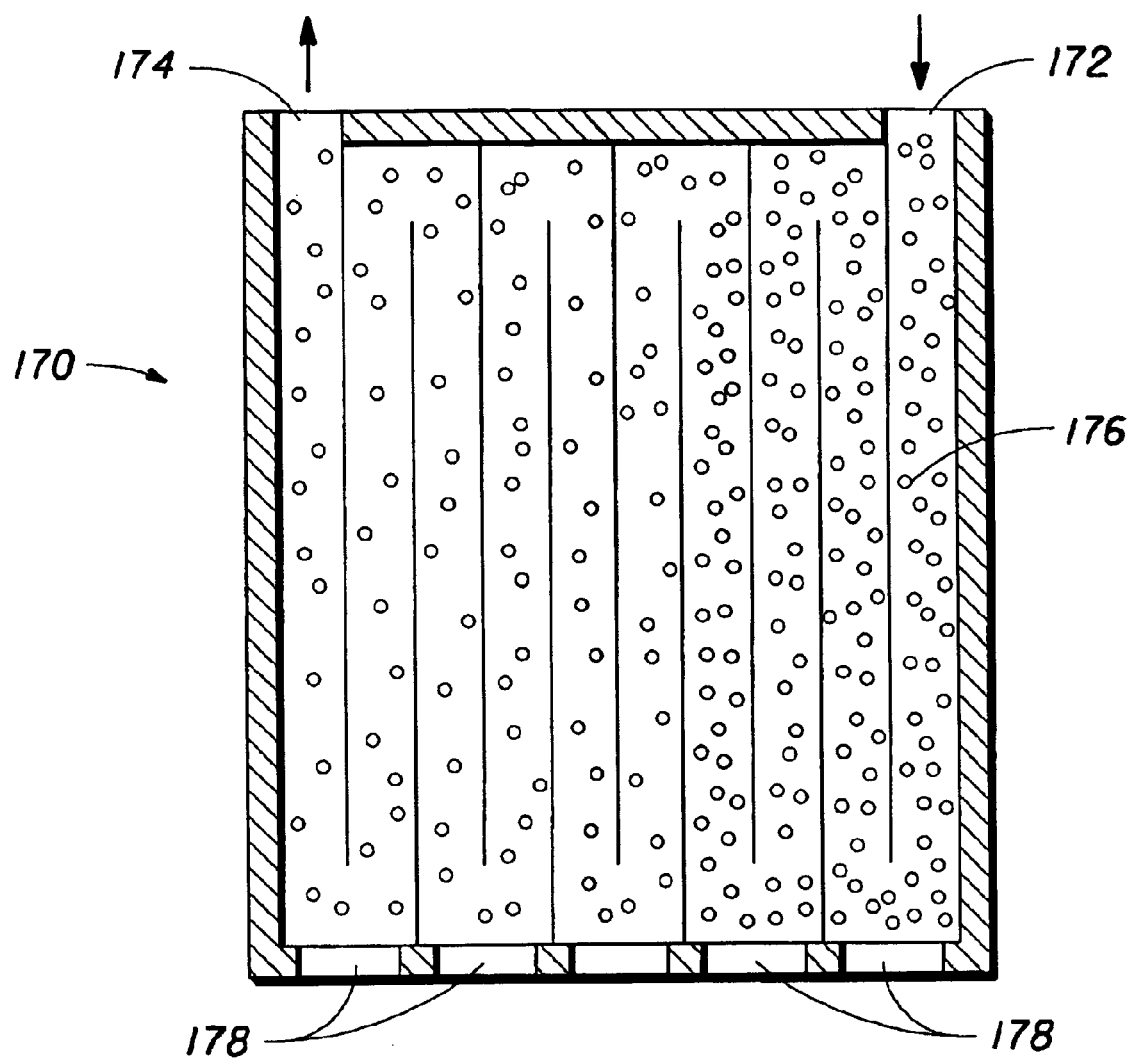
FIGS. 13A–C are schematic views of deionization beds arranged to display a color change that indicates the extent to which the beds are spent.
Figure 13B:
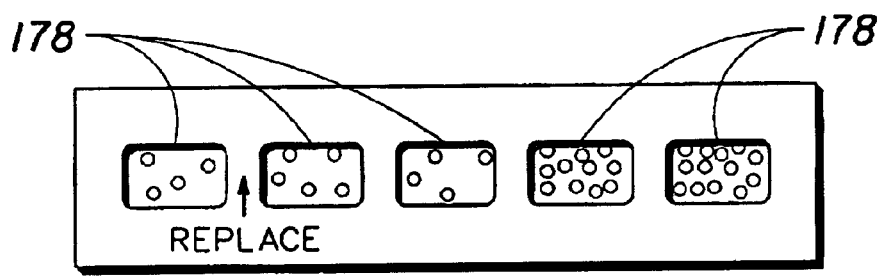
Figure 13C:
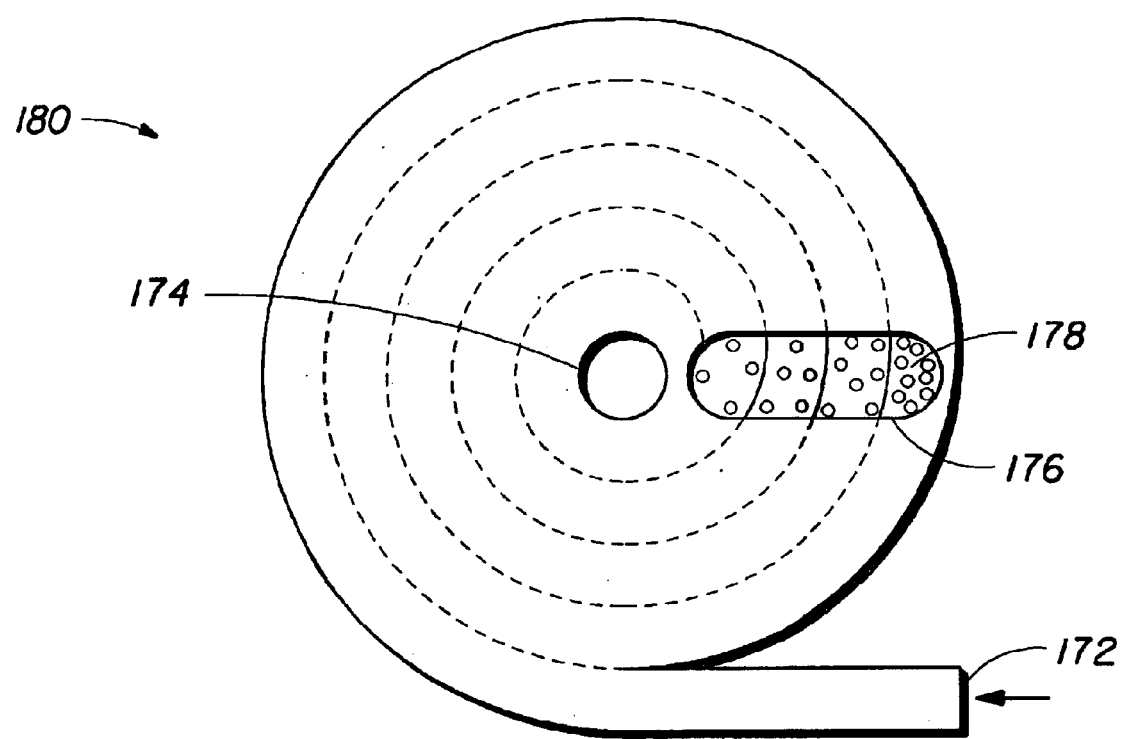

FIGS. 13A–C are schematic views of deionization beds arranged to outwardly display a color change that indicates to individual users of the device the extent to which the beds are exhausted. Suitable deionization materials that change color upon exchanging ions include MBD-12 and MBD-30 Self Indicating Mixed Bed Resins (available from Resintech, Inc. of Cherry Hill, N.J.) and IONAC NM-65 Indicator Mixed Bed Resin (available from Sybron Chemicals Inc. of Birmingham, N.J.). Such color changes may be due to the presence of an indicator dye in, on or around the deionization materials. While many arrangements of a deionization bed adjacent a clear sight glass are possible, it is preferred that the deionization bed form an elongated column having a high aspect ratio (i.e., a length many times the width). In this manner, the deionization materials closest to the column inlet exchange ions first and the material downstream will not be significantly used until the material upstream of it is fully exchanged. Therefore, there is a fairly distinct region of the column that is carrying out the deionization at any one time and this region propagates along the length of the column as the material gets used. Since a deionization material with a color change indicator is used, there is a color change that propagates along the column. By arranging the column in a manner where a plurality of serially spaced apart segments of the column pass under a sight glass, a display can be provided that allows a rapid indication of use. Preferably, the sight glass is marked with a "replace deionizing bed" instruction adjacent one of the later column segments viewable through the sight glass. While the foregoing arrangement has been described with regard to a deionization bed, a similar arrangement, color indicator and sight glass maybe used to prepare a lead removal unit.

In FIG. 13A, a side view shows that the deionization column 170 is arranged in an elongated serpentine pattern having an inlet 172, an outlet 174, deionization material 176 disposed there between, and a sight glass 178 adjacent one end of the serpentine. FIG. 13B is an end view of the column 170 showing the display formed by the sight glasses. For example, an individual user would quickly notice that the present column was two-fifths spent and that the column should be replaced when the column becomes four-fifths spent in order to prevent breakthrough of ions that could then reach and damage the electrocatalysts or the PEM. While the display is shown as a segmented array of sight glasses it is equally suitable to have a continuous sight glass along the end. FIG. 13C is a side view of an alternative column arranged in an spiraling pattern having an inlet 172, an outlet 174, deionization material 176, and a sight glass 178 extending over downstream segments of the column. While the segments here do not represent equal fractions of the column, the display is still effective to instruct the individual user when to change out the column with a new column.

Figure 14:
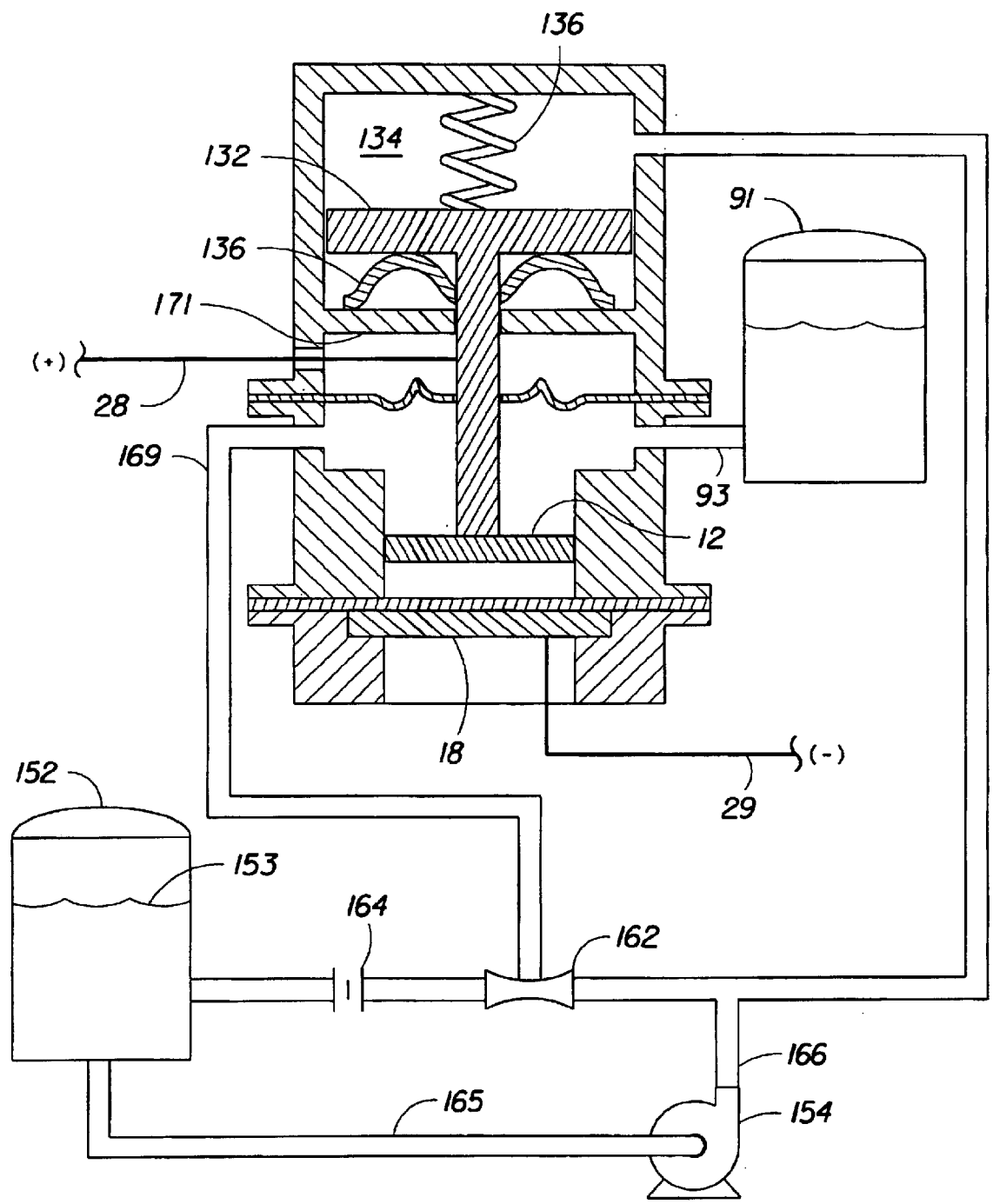
FIG. 14 is a schematic side view of an electrochemical apparatus having a separate deionized water reservoir in fluid communication with the anode.
Figure 15A:
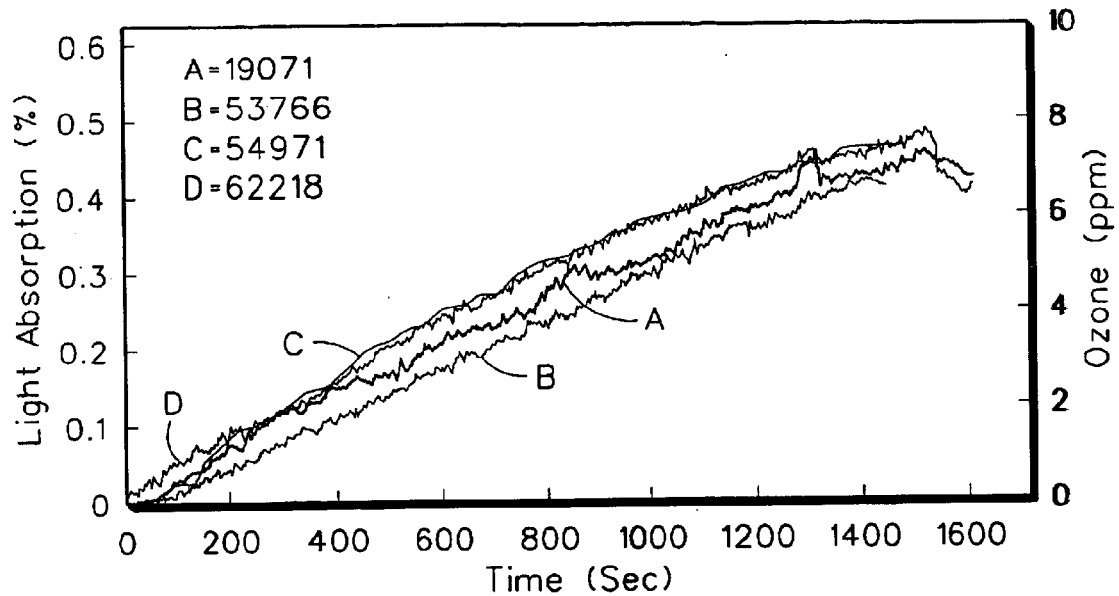
FIGS. 15A–D are graphs of percent light absorption as a function of time in seconds for electrochemical cells built according to FIG. 7 and operated over many repetitive cycles.
Figure 15B:
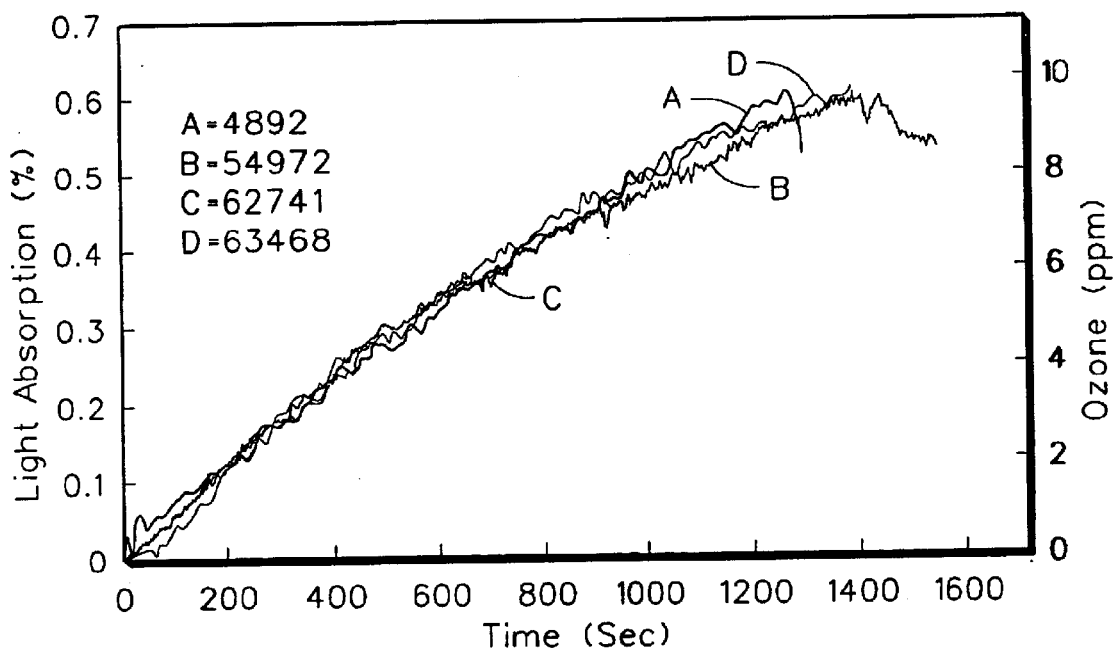
Figure 15C:
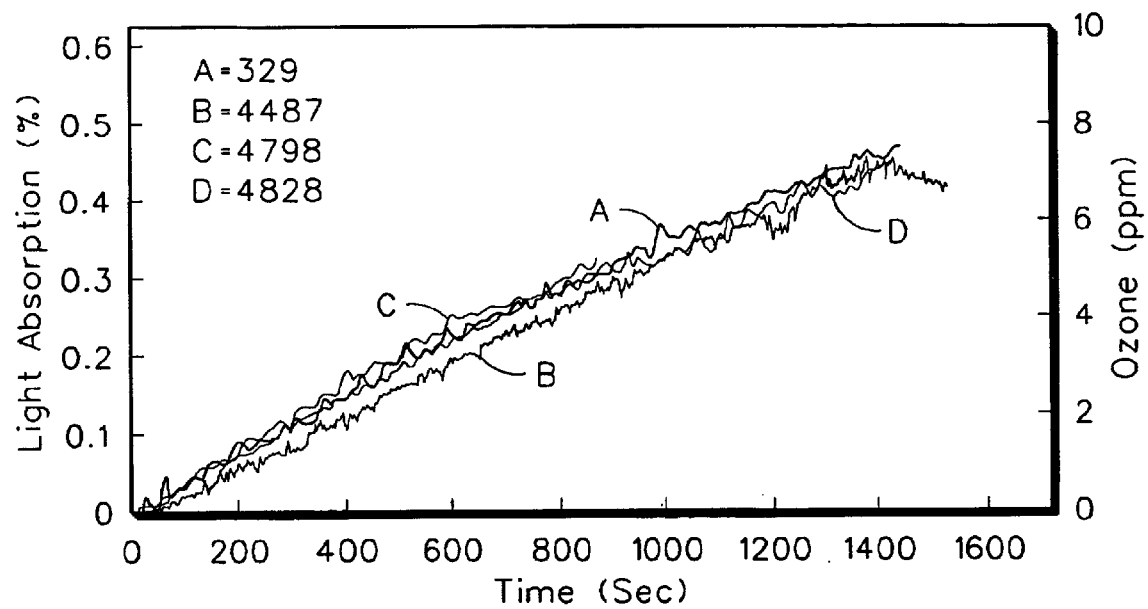
Figure 15D:
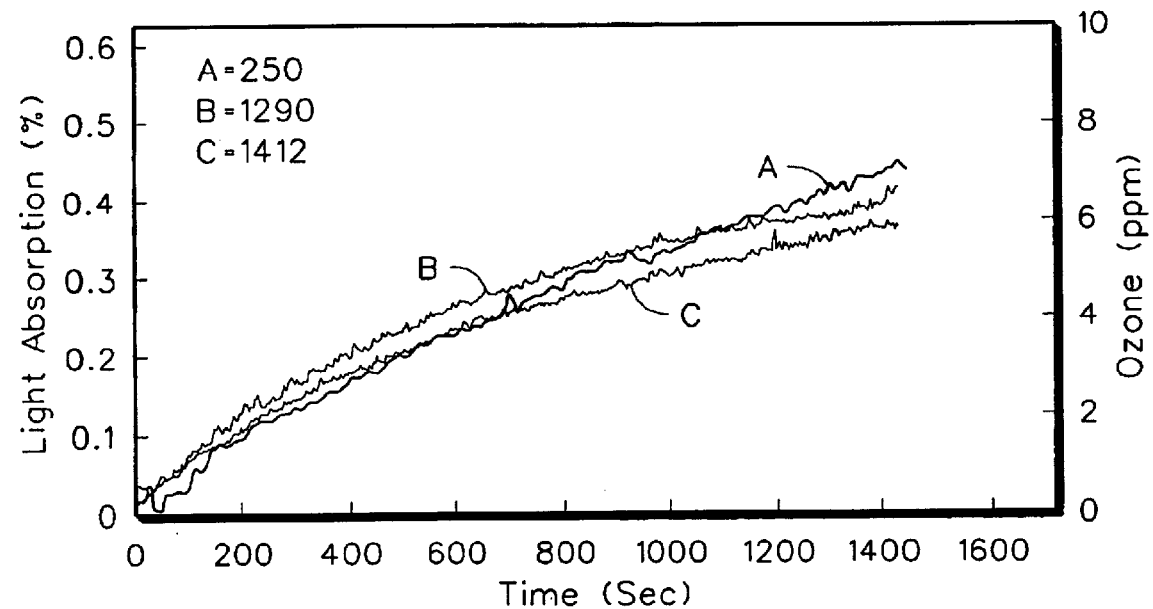

FIG. 14 is a schematic side view of an electrochemical apparatus using deionized water from a reservoir 91 rather than using process water from reservoir 152. As with FIGS. 7B–C, the use of prepackaged deionized water 91 eliminates the threat of contaminating the anode and PEM such that filtration and deionization devices are not needed within the apparatus. Here, the process water 153 is pressurized by pump 154 and delivered to the back of the piston 132 for actuating the mobile electrode and through the venturi 162 to draw ozone gas into the process water. Preferably, the anode chamber is arranged with the water conduit 93 such that the level of deionized water remains below the ozone exit port 169. It is also preferred that the anode chamber have sufficient headspace to allow for phase separation of the ozone/oxygen gas from the water, such that only the gas phase is drawn through port 169 to the venturi 162. A seal or diaphragm is provided around the push rod 48 to prevent passage of the pressurized process fluid acting upon the piston from getting into the anode chamber. As shown, the diaphragm 171 defines the upper limit of the anode chamber.

Figure 18A:
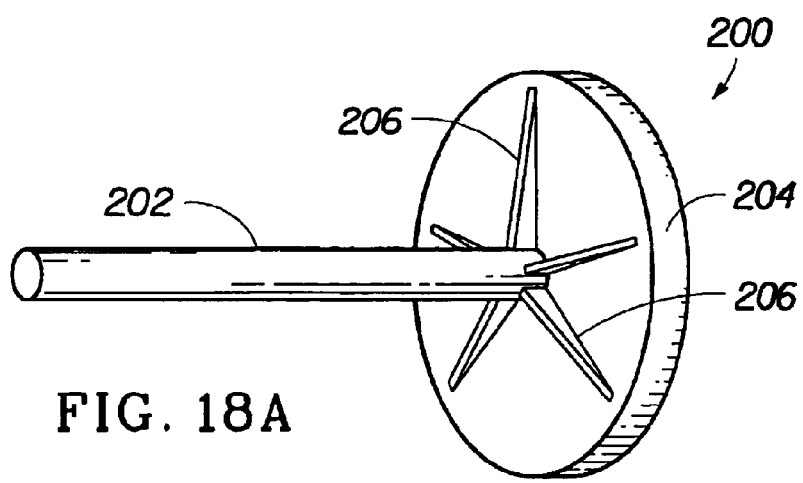
FIGS. 18A–C are perspective views of retractable electrodes coupled to a shaft, wherein the electrode has been modified to improve the current distribution/collection across the face of the electrode.
Figure 18B:
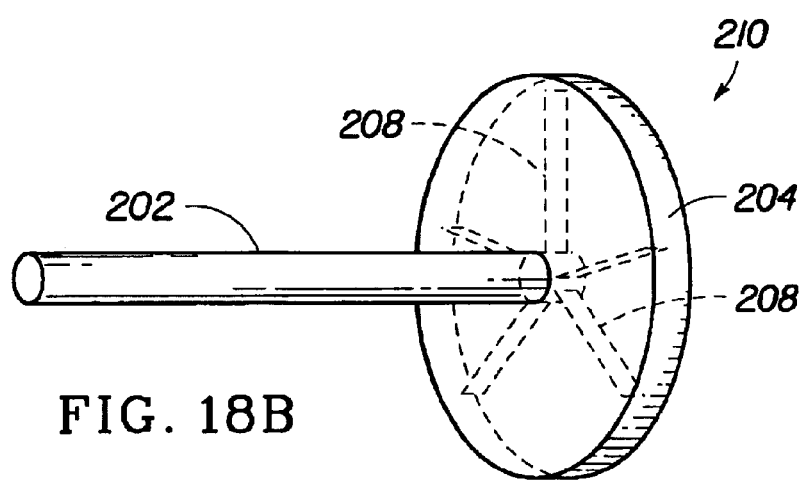
Figure 18C:
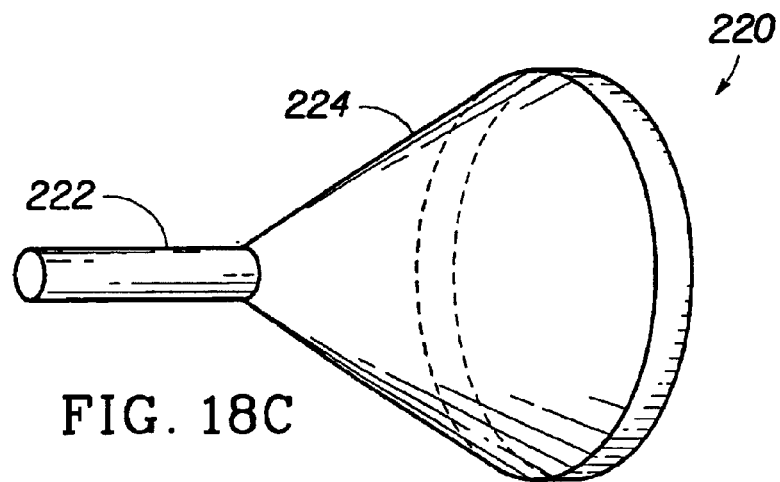

FIGS. 18A–C are perspective views of retractable electrodes coupled to a shaft, wherein the electrode has been modified to improve the current distribution/collection across the face of the electrode. FIG. 18A illustrates an electrode 200 having a set of electronically conducting ribs 206, preferably metal, that are formed into a radial pattern on the back surface of the anode substrate 204 in order to improve current distribution or collection from the electronically conducting shaft 202 across the face of the electrode substrate 204. This design improves current distribution without blocking the surface area of the anode substrate or increasing the thickness of the porous anode substrate. FIG. 18B illustrates an electrode 210 having a set of fully embedded electronically conducting members 208 disposed radially from the shaft 202. In both FIGS. 18A and 18B, the electronically conducting members 206, 208 are formed within the porous substrate 204. Preferably, the electronically conducting members are disposed within a metal powder and pressed together under substantial pressure to form a "green body." The green body is then transferred into a furnace for sintering the substrate 204. FIG. 18C illustrates an electrode 220 having a less preferred conical substrate 224 coupled to the shaft 222, wherein the increased thickness of the substrate increases the current distribution or collection across the face of the anode. Unfortunately, the increased thickness also increases the distance that anode reactants and products must diffuse.

EXAMPLE 1

Porous titanium substrates, namely pieces of a woven titanium cloth (150×150 per inch, clean, 0.0027" wire diameter, twill weave, 35.4% open area; Unique Wire Weave, Hillside, N.J. 07205), were pretreated and subsequently electroplated with β-lead dioxide. A number of these plead dioxide-coated titanium cloths were used in an electrochemical cell incorporating a commercially available proton exchange polymer membrane (sold under the trade name Nafion®, by E. I. du Pont de Nemours and Company, Wilmington, Del. 19898), which is a perfluorosulfonic acid solid polymer electrolyte, and tested using an apparatus described in U.S. Pat. No. 5,460,705 commonly owned by the applicant. In some cases, the β-lead dioxide-coated titanium cloths were mechanically pressed against one side of a proton exchange membrane sample simply by means of clamping together the endplates of the electrochemical cell. In other cases, the β-lead dioxide-coated titanium cloths were hot pressed onto one side of similar samples of a proton exchange membrane. Hot pressing involved placing a sandwich structure, consisting of the cation exchange membrane, the β-lead dioxide-coated titanium cloth anode electrode, and a platinum-supported carbon catalyzed carbon cloth gas diffusion electrode on either side of the membrane between the platens of a hot press preheated to 100° C. and pressing at approximately 100 psi. The temperature of the platens was then raised to 120° C. and a pressure of 2,500 psi was applied for 90 seconds.

On testing the performance of electrochemical cells containing β-lead dioxide-coated titanium cloth electrodes bonded to cation exchange polymer membranes by either method, it was found that the ozone gas content in the evolved ozone/oxygen gas stream decreased from an initially high value of 12–15 wt % to a value of the order of 1–2 wt % over a period of time of the order of 12–24 hours. Further, cell voltages decreased from initially high values of the order of 4–6 volts to a value of the order of 1–2 volts. In addition, upon dismantling tested electrochemical cells that contained β-lead dioxide-coated titanium cloth as the anode substrate/anode electrocatalyst material, the surface of the proton exchange polymer membrane in contact with the β-lead dioxide electrocatalyst layer had regions covered with a milky white liquid substance. The surface of the proton exchange polymer membrane in contact with the platinum-supported carbon cathodic electrocatalyst layer displayed dendrithic or fractal-like growths of a material within the membrane.

While the nature of these materials on the surfaces of the proton exchange polymer membranes were not determined, it is proposed that the following processes took place on testing these electrochemical cells for electrochemical ozone evolution. The individual wire strands that made up each woven titanium cloth sample was electroplated with lead dioxide over the entire circumference of the cylindrically shaped wire strands. However, when the β-lead dioxide-coated titanium cloth samples were bonded to the surfaces of proton exchange membrane samples, either by mechanical pressing on clamping the end plates or by hot pressing, only a fraction of the entire surface area of the β-lead dioxide electrocatalyst layer was in contact and embedded into the proton exchange polymer membrane material.

On operating an electrochemical cell containing such an anodic substrate/electrocatalyst layer, parts of the β-lead dioxide electrocatalyst layer not in contact with the proton exchange polymer membrane slowly dissolved in the presence of the highly acidic environment that exists at the anode surface under electrochemical ozone evolution conditions. Some of the dissolved β-lead dioxide, in the form of $Pb^{2+}$ cations, migrated through the cation exchange polymer membrane to the surface of the cathode, under the presence of the applied electric field, where they were reduced to metallic lead atoms. Gradually, build up of atom-upon-atom of lead metal gave rise to a dendrithic growth of electrodeposited lead metal from the surface of the cathode through the proton conducting channels that are known to exist in proton exchange polymer membranes to the surface of the anode. Eventually, the proton exchange polymer membrane became a mixed ionic/electronic conductor with increasing electronic conductivity character as the time of electrochemical ozone evolution increased. This accounts for the decrease in cell voltage observed with increasing time of electrolysis.

Because the woven titanium cloth consisted of fine cylindrical titanium wires, subsequent contact of these β-lead dioxide-coated titanium wires with the surface of the proton exchange polymer membrane led to localized point contacts embedded into the surface of the membrane, particularly at points corresponding to the overlap of the woven wires. Thus, although the average current density applied to the electrochemical cells on carrying out the various tests were 1 A $cm^{-2}$ on average, it is very likely that the local real current density applied at the point contacts could be of the order of 5–10 A $cm^{-2}$. The combination of heating effects (associated with the high local current density) with the highly oxidizing environment (associated with ozone evolution) gave rise to local degradation of the proton exchange membrane. This is in keeping with the observation of a milky white liquid substance on the surface of the proton exchange polymer membrane in contact with the β-anodic lead dioxide electrocatalyst layer. In all cases, electrochemical tests involving β-lead dioxide-coated titanium cloth anodes were carried out using deionized water circulated between a reservoir and the electrochemical cell, where the temperature of the water was maintained at 30±3° C.

EXAMPLE 2

Another type of porous titanium substrates, namely sintered porous titanium substrates derived from the sintering of regular shaped titanium powders (e.g., spheres) or irregular shaped titanium particles under high temperature and pressure in an inert gas environment and available from Astro Met, Inc., Cincinnati, Ohio 45215 (100-80/120 and 100-45/60; 5.5"×11"×0.050" sheets) and Mott Corporation, Farmington, Conn. 06032 (Mott 40 micron and Mott 20 micron), respectively, were used. The sintered porous titanium substrates were pretreated and subsequently electroplated with β-lead dioxide as described above for the titanium cloth samples. The β-lead dioxide-coated sintered porous titanium substrates were mechanically pressed against one side of samples of a proton exchange polymer membrane (Nafion®) on clamping the endplates of an electrochemical cell together. They were tested under identical conditions to those utilized for the β-lead dioxide-coated titanium cloth anodic substrates. The thickness of the porous titanium substrates was in the range 0.040"–0.075" and it was observed that these substrates had very flat parallel surfaces. β-lead dioxide was deposited on only one surface of the sintered porous titanium substrates which formed a uniform coating covering the whole surface of each substrate.

On testing β-lead dioxide-coated sintered porous titanium substrates for electrochemical ozone evolution, it was found that electrochemical cells containing these anodic substrates/electrocatalyst layers could produce ozone at high concentrations of the order of 12 to 15 wt % for seemingly indefinite periods of time, so long as such electrochemical cells remained under compression and an applied current density of 1.0–1.6 A cm$^{-2}$ was impressed on the electrodes from an external DC power source. Cell voltages of 3.5–5.5 V were observed on flowing deionized water between the electrochemical cell and a reservoir at a temperature of 30±3° C. The unexpected result of the continuous production of high weight percent ozone for an extended period of time is attributed to the fact that the sintered porous titanium substrates have flat planar surfaces. Thus, the β-lead dioxide layer on such surfaces is also flat resulting in all of the exposed surface area of the Plead dioxide layer being in contact with the surface of the proton exchange polymer membrane, and under electrochemical operating conditions, having a voltage greater than 3.0 V applied across the plead dioxide/proton exchange polymer membrane interface. As indicated in FIG. 1, under such circumstances, β-lead dioxide should be stable indefinitely.

Figure 17A:
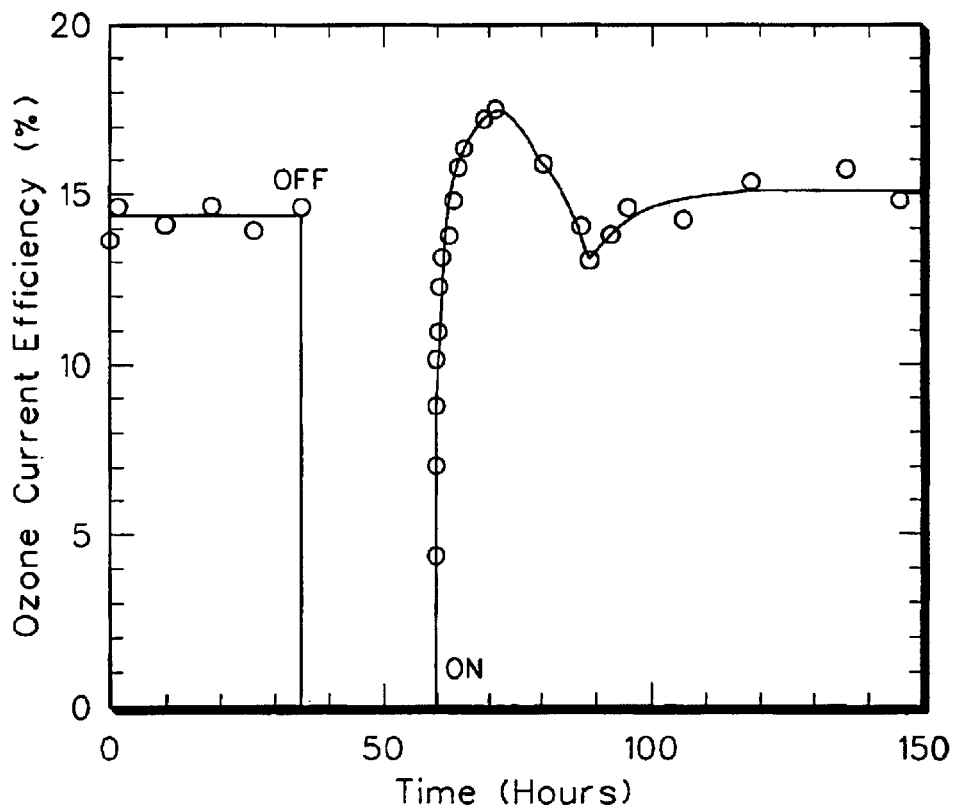
FIGS. 17A–B are graphs of ozone current efficient in percent as a function of time of a period in which the ozone generator is cycled on and off.
Figure 17B:
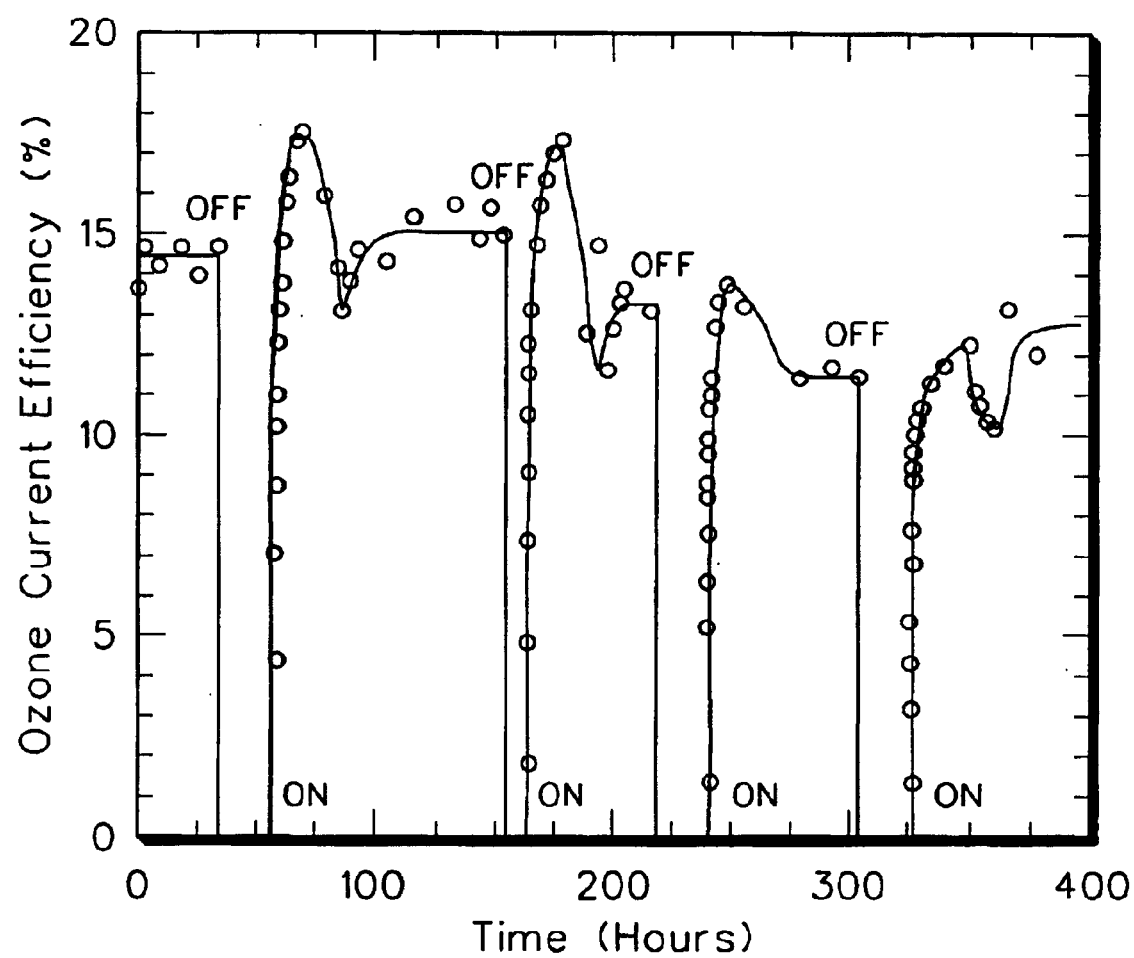

EXAMPLE 3

β-lead dioxide coated sintered porous titanium substrates were subjected to multiple applied current density "on"/"off" events, leading to a gradual lowering of the ozone current efficiency. For coated substrates that were maintained continuously in compression with the proton exchange polymer membrane, both in the case when the applied current density was "on" and when the applied current density was "off," the effect of four applied current density "on"/"off" events on the ozone current efficiency for an electrochemical cell initially producing ozone at a current efficiency of 14.5 (corresponding to a concentration of 14.5 wt %) is presented in FIGS. 17A–B. It was further observed that the dramatic effect of applied current density "on"/"off" events on ozone current efficiency was more pronounced for electrodes having low electrocatalyst loadings of β-lead dioxide. For instance, for β-lead dioxide loadings of 5–10 mg cm$^{-2}$, 2–3 applied current density "on"/"off" events reduced the ozone production capability of the electrochemical cell from 10–12 wt % to less than 2 wt %. For an electrode with a β-lead dioxide loading of 80 mg cm$^{-2}$, an ozone production capability of the order of 5 wt % was obtained after 9 applied current density "on"/"off" events.

Degradation in ozone production performance as a result of time intervals while no current density is impressed upon the electrodes is suggested by the data presented in FIG. 1. This figure clearly shows that for the lead-water system at low electrode potentials, that is, when no anodic current is flowing through the electrode/electrolyte interface, Pb$^{2+}$ ions are the most stable species in acidic environments. Maintaining a β-lead dioxide-coated sintered porous titanium substrate in contact with an acidic proton exchange polymer membrane when no current is flowing through an electrochemical cell will give rise to degradation of the β-lead dioxide electrocatalyst layer which subsequently hinders, or reduces, its ability to evolve ozone gas on reimpressing a current between the β-lead dioxide-coated anode and a cathode.

Under the conditions of no applied electric field, that is, when the current density impressed on the electrodes is turned "off," dissolution/precipitation processes involving $PbO_2/Pb^{2+}$ are likely to take place at the β-lead dioxide/proton exchange polymer membrane interface. In the absence of an applied electric field during current "off" events, there is no driving force for the migration of Pb$^{2+}$ ions into the proton conducting polymer membrane towards the surface of the cathode unlike the situation described above for the β-lead dioxide-coated titanium cloth.

EXAMPLE 4

An experimental setup was prepared including four electrochemical cells to test whether the removal of β-lead dioxide-coated porous anodic substrates from being in contact with proton conducting polymer membranes, during time intervals when no current is flowing between the anode and cathode, would significantly increase the lifetime of such electrochemical cells and maintain high ozone production rates when an applied current density is reimpressed on the electrodes after a current "off" event. However, this solution is only applicable to porous anodic substrates that have flat planar surfaces as described above in the second example which involved the use of sintered porous titanium substrates. The proposed solution, which is the basis of the invention disclosed in this patent application, will not be effective in the case of porous anodic substrates that have only portions of the surface area of a layer, or regions of the surface of a layer, of β-lead dioxide anodic electrocatalyst in contact with the proton exchange polymer membrane when the electrocatalyst-coated porous substrate and the membrane are compressed together in an electrochemical cell.

Porous anodic substrates that would be ineffective are those that have a relatively small thickness (less than 0.010" thick) and have a layer of β-lead dioxide electrocatalyst material on a front or first surface, around the entire perimeter of fine wires, on walls of large pores readily accessible to water and on a back or second surface. A representative example of such porous substrates was described above in the first example and involved the use of porous woven titanium cloth. Other ineffective porous substrates would include non-woven cloths, woven or non-woven meshes, screens, perforated thin metal sheets, or thin metal sheets with microetched holes. However, if the β-lead dioxide electrocatalyst layer is deposited on only those regions of the surface, segments of the surface or portions of the exposed surface area of woven or non-woven cloths, woven or non-woven meshes, screens, perforated thin metal sheets, or thin metal sheets with microetched holes that are in contact with a proton exchange polymer membrane when such plated porous anodic substrates and membrane specimens are under compression in electrochemical cells, then the proposed solution is as effective for these substrates as it is for sintered porous metal or ceramic substrates described in the second example above.

An apparatus and method for retracting a β-lead dioxide-coated porous anodic substrate from making contact with a proton conducting polymer membrane and for subsequently having the ability n of placing such a β-lead dioxide-coated porous anodic substrate back in contact with the proton conducting polymer membrane was prepared in accordance with FIG. 7. In particular, the apparatus and method of the invention must be capable of retracting all of the exposed surface area of the β-lead dioxide coating on a porous anodic substrate from making contact with a proton exchange polymer membrane specimen in an electrochemical cell during a current "off" event. Similarly, the apparatus and method of the invention must be capable of placing all of the exposed surface area of the β-lead dioxide coating on a porous anodic substrate in contact with a proton exchange polymer membrane specimen in an electrochemical cell during a current "on" event.

The cathode and PEM were stationary with only the porous titanium anode substrate and lead dioxide electrocatalyst coupled to the end of an electrically operated solenoid actuator. The solenoid actuator pushed the anode substrate/electrocatalyst into compressed contact with the PEM and a pair of springs raised the anode substrate/electrocatalyst away from the PEM. A controller was used to control each of the four electrochemical cells at a given duration and frequency of operation. Each of the cells was operated without switching off the power. However, the cells were turned "off" by retracting the anode out of contact with the PEM/cathode, since the non-ionically conducting deionized water effectively provided an open circuit. Cell #1 was operated in a cycle of 1.5 minutes "on" and 1.5 minutes "off". Cell #2 was operated in a cycle of 25 minutes "on" and 10 minutes "off". Cell #3 was operated in a cycle of 25 minutes "on" and 2 hours "off". Cell #4 was operated in a cycle of 26 minutes "on" and 24 hours "off". A control cell was operated in which the power was switched off during periods when the anode was retracted, but the results showed no significant difference in performance relative to cells having the power on continuously.

The ozone gas concentration produced by each of the four electrochemical cells was measured using an Ocean Optics UV absorption system and software to monitor the absorption of UV light by dissolved ozone in the deionized water surrounding the cell. FIGS. 15A–D show the light absorbance that was measured periodically after large numbers of operating cycles had been performed for cells 1–4, respectively. The legend in each figure indicates the number of operating cycles at which the dissolved ozone concentration was tested. For each test, the figures plot percentage light absorption as a function of time in seconds for a period of about 1500 seconds. Each of the charts in FIGS. 15A–D show that very little decline in ozone production occurred despite 62,218; 63,468; 4,826 and 1,412 operating cycles in cells 1–4, respectively.

EXAMPLE 5

Figure 16:
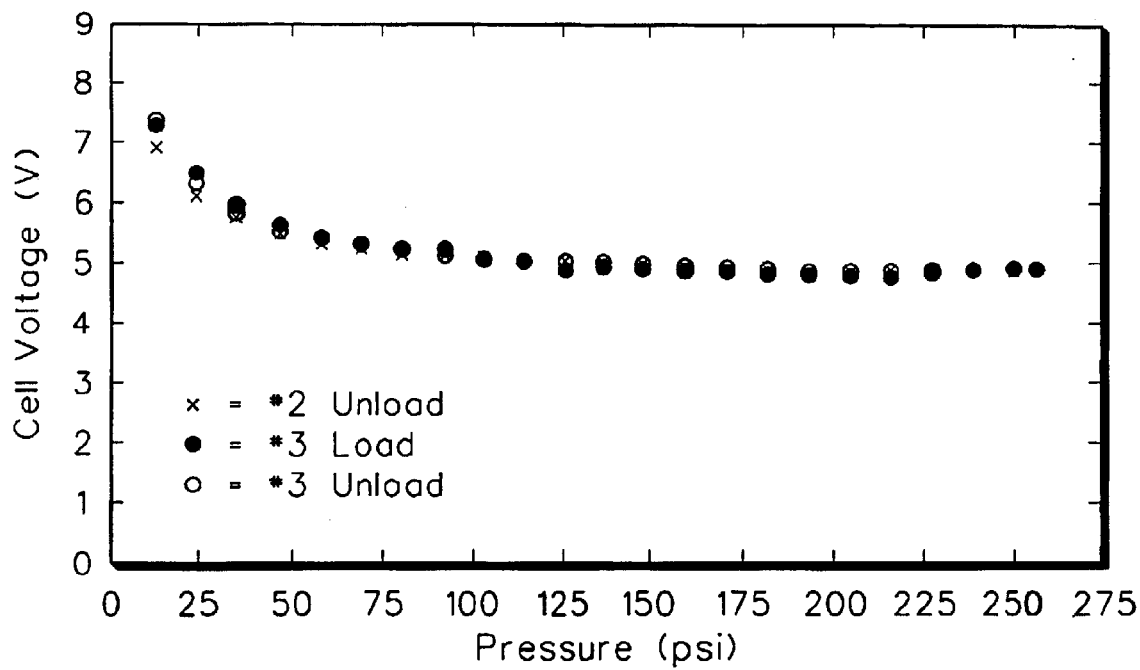
FIG. 16 is a graph of cell voltage as a function of pressure in psi for the electrochemical cell of FIG. 8.

An electrochemical cell was prepared in accordance with FIG. 8 and the cell voltage was measured as the compression between the electrodes was varied between about 10 psi and about 260 psi. FIG. 16 is a graph of the resulting cell voltage as a function of pressure in psi for the electrochemical cell. The graph shows that cell voltage declines rapidly with increasing pressure up to a pressure of about 50 psi. At pressures above 50 psi, additional pressure produced very little decline in cell voltage.

While the foregoing is directed to the preferred embodiment of the present invention, other and further embodiments of the invention may be devised without departing from the basic scope thereof, and the scope thereof is determined by the claims that follow.

What is claimed is:

1. An electrochemical apparatus, comprising:
   at least one electrochemical cell having first and second electrodes and an ion exchange membrane disposed between the first and second electrodes,
   a power source for applying a voltage between the first and second electrodes, and
   means for automatically retracting one or more of the first and second electrodes out of contact with the ion exchange membrane.

2. The electrochemical apparatus of claim 1, wherein the means for automatically retracting is passive.

3. The electrochemical apparatus of claim 2, wherein the passive means for automatically retracting is a stored energy device.

4. The electrochemical apparatus of claim 3, wherein the stored energy device is selected from a spring, gravity, hydraulic accumulator, pneumatic accumulator, or combinations thereof.

5. The electrochemical apparatus of claim 1, wherein the one or more of the first and second electrodes includes material that is unstable or deactivates in the presence of the ion exchange membrane without applying a voltage.

6. The electrochemical apparatus of claim 5, wherein the material is lead dioxide.

7. The electrochemical apparatus of claim 6, characterized in that the lead dioxide maintains its activity during repetitive cycling of the power source.

8. The electrochemical apparatus of claim 1, further comprising:
   a pump for delivering water to the at least one electrochemical cell, wherein the means for retracting is a hydraulic actuator in fluid communication with the water.

9. The electrochemical apparatus of claim 8, further comprising means for introducing ozone into a separate system.

10. The electrochemical apparatus of claim 9, wherein the ozone comprises dissolved ozone in water, an ozone/oxygen gas stream, or combinations thereof.

11. The electrochemical apparatus of claim 1, wherein the ion exchange membrane and one of the electrodes are stationary.

12. The electrochemical apparatus of claim 11, wherein the stationary electrode is a cathode.

13. The electrochemical apparatus of claim 1, wherein the at least one electrochemical cell is a plurality of electrochemical cells.

14. The electrochemical apparatus of claim 13, wherein the plurality of electrochemical cells form a stack of electrochemical cells.

15. The electrochemical apparatus of claim 1, further comprising:
   a lead-containing catalyst disposed on one or more of the first and second electrodes; and
   a lead removal device in fluid communication with the at least one electrochemical cell.

16. The electrochemical apparatus of claim 15, wherein the lead removal device contains a material known to bind or adsorb lead ions, particulates or colloidal species.

17. The electrochemical apparatus of claim 16, wherein the material is selected from a zeolite, alumina, silica, or mixtures thereof.

18. The electrochemical apparatus of claim 16, wherein the material is in powdered or granulated form.

19. The electrochemical apparatus of claim 1, wherein the one or more of the first and second electrodes are retracted out of contact with the ion exchange membrane when no voltage is being applied between the first and second electrodes.

20. The electrochemical apparatus of claim 1, wherein the means for retracting the one or more electrodes further comprises a guide member to align the electrodes.

21. The electrochemical apparatus of claim 1, wherein the means for retracting the electrodes is coupled to the one or more of the first and second electrodes by a positioning rod.

22. The electrochemical apparatus of claim 21, further comprising an electrode chamber having a liquid impermeable diaphragm sealing the chamber and moving along with the positioning rod.

23. The electrochemical apparatus of claim 1, further comprising:
   means for positioning the first and second electrodes in contact with the ion exchange membrane.

24. The electrochemical apparatus of claim 23, wherein the first electrode is coupled to the means for positioning and the first electrode has an electrocatalyst formed only on surfaces of the first electrode that are disposed to make contact with the ion exchange membrane.

25. The electrochemical apparatus of claim 24, wherein the second electrode is stationary.

26. The electrochemical apparatus of claim 25, wherein the ion exchange membrane is secured onto the second electrode.

27. The electrochemical apparatus of claim 23, wherein the means for positioning is selected from a hydraulic actuator, a pneumatic actuator, manual mechanical means, piezo-electric means, electric motor means, or combinations thereof.

28. The electrochemical apparatus of claim 23, further comprising:
   a pump for delivering water to the at least one electrochemical cell, wherein the means for positioning is a hydraulic actuator in fluid communication with the water.

29. The electrochemical apparatus of claim 23, wherein the means for positioning provides a compressive force against the ion exchange membrane generally greater than 15 psig.

30. The electrochemical apparatus of claim 23, wherein the compressive force is between 5 and 100 psig.

31. The electrochemical apparatus of claim 23, wherein the means for retracting overcomes the means for positioning when the power source is off.

32. The electrochemical apparatus of claim 23, wherein the means for positioning overcomes the means for retracting when the power source is on.

33. The electrochemical apparatus of claim 23, wherein the means for positioning the electrodes further comprises a guide member to align the electrodes.

34. The electrochemical apparatus of claim 23, wherein the means for positioning the electrodes is coupled to the one or more of the first and second electrodes by a positioning rod.

35. The electrochemical apparatus of claim 34, further comprising an electrode chamber having a liquid impermeable diaphragm sealing the chamber and moving along with the positioning rod.

36. The electrochemical apparatus of claim 34, wherein the positioning rod comprises an electronic conductor communicating between a voltage source and the one or more of the first and second electrodes.

37. The electrochemical apparatus of claim 23, further comprising a water reservoir in fluid communication with an inlet to the pump and in fluid communication with an outlet from the at least one electrochemical cell.

38. The electrochemical apparatus of claim 37, further comprising a recirculation conduit from an outlet of the pump back to the water reservoir.

39. The electrochemical apparatus of claim 38, further comprising means for apportioning the amount of water pumped to the at least one electrochemical cell and the amount of water recirculated back to the water reservoir.

40. The electrochemical apparatus of claim 23, further comprising an ion exchange bed disposed upstream of the at least one electrochemical cell.

41. The electrochemical apparatus of claim 40, further comprising an ozone destruct catalyst upstream of the ion exchange bed.

42. The electrochemical apparatus of claim 23, wherein the at least one electrochemical cell is a fuel cell.

43. The electrochemical apparatus of claim 1, wherein the ion exchange membrane is a cation exchange membrane.

44. An electrochemical apparatus, comprising:
   an electrochemical cell having first and second electrodes and electrolyte disposed between the first and second electrodes,
   a power source for applying a voltage between the first and second electrodes,
   means for selectively positioning one or more of the first and second electrodes into contact with the electrolyte; and
   means for retracting the one or more of the first and second electrodes out of contact with the electrolyte when the means for selectively positioning is turned off.

45. A method of operating an electrochemical cell having first and second electrodes and electrolyte disposed between the first and second electrodes, comprising:
   (a) automatically separating one or more of the first and second electrodes from the electrolyte upon one or more standby conditions, wherein the electrolyte is an ion exchange membrane.

46. THe method of claim 45, wherein the one or more standby conditions is selected from a voltage os less than one Volt being applied between the first and second electrodes, expiration of a time period, an ozone concentration greater than a setpoint ozone concentration, contact pressure of less than 10 psig, or combinations thereof.

47. The method of claim 45, further comprising:
   (b) automatically positioning the one or more of the first and second electrodes into contact with the electrolyte upon one or more production conditions.

48. The method of claim 47, wherein the one or more production conditions is selected from a voltage greater than one Volt being applied between the first and second electrodes, expiration of a time period, an ozone concentration less than a setpoint ozone concentration, contact pressure greater than 10 psig, or combinations thereof.

49. The method of claim 47, wherein the electrolyte is a polymer electrolyte membrane, and wherein the step of automatically positioning comprises compressing the one or more of the first and second electrodes against the polymer electrolyte membrane with a compressive force between 5 and 100 psig.

50. The method of claim 49, wherein the compressive force is between 25 and 70 psig.

51. The method of claim 47, further comprising:
   applying a voltage between the first and second electrodes.

52. The method of claim 51, further comprising:
   turning on a water pump.

53. THe method of claim 52, further comprising:
   automatically positioning the one or more of the first and second electrodes into contact with the electrolyte upon one or more production conditions.

54. At least one electrochemical coil including a cathode electrode, an anode electrode, an acidic electrolyte disposed between the anode electrode and the cathode electrode, and a power source for applying a voltage between the anode electrode and the cathode electrode, characterized in that the anode electrode has a layer of lead dioxide electrocatalyst facing the acidic electrolyte, a retractor mechanism being provided which is responsive to one or more predetermined standby conditions to retract the anode electrode from an initial position in which the lead dioxide electrocatalyst is in contact with the electrolyte to a retracted position in which the lead dioxide electrocatalyst is spaced from the electrolyte.

55. The at least one electrochemical cell of claim 54 wherein the retractor mechanism is a passive retraction mechanism.

56. The at least one electrochemical cell of claim 54 wherein the lead dioxide electrocatalyst is β-lead dioxide, α-lead dioxide, or a combination thereof.

57. The at least one electrochemical cell of claim 54 wherein the acidic electrolyte is a proton exchange membrane.

58. The at least one electrochemical cell of claim 57, wherein the one or more standby conditions includes a contact pressure of less than 10 psig of the anode electrode with the proton exchange membrane.

59. The at least one electrochemical cell of claim 57 further comprising an actuator for moving the anode electrode from the retracted position back to the initial position in response to one or more production conditions including a contact pressure of greater than 10 psig of the anode electrode with the electrolyte.

60. The at least one electrochemical cell of claim 54 wherein the acidic electrolyte is an aqueous solution of a dissolved inorganic acid, a dissolved organic acid, or a mixture thereof.

61. The at least one electrochemical cell of claim 54, wherein the one or more standby conditions are selected from:
a voltage of less than one volt being applied between the first and second electrodes, the expiration of a time period of operation of the cell, an ozone concentration greater than a set point ozone concentration within the cell, no anodic oxygen/ozone evolution reactions occurring, and no current flowing through the cell.

62. The at least one electrochemical cell of claim 54 further comprising an actuator for moving the anode electrode from the retracted position back to the initial position in response to one or more production conditions.

63. The at least one electrochemical cell of claim 62 wherein the one or more production conditions are selected from:
a voltage greater than one volt being applied between the first and second electrodes, the expiration of a time period from termination of operation of the cell, and an ozone concentration less than a set point ozone concentration within the cell.

64. The at least one electrochemical cell of claim 62 wherein the retractor mechanism and the actuator are constituted by a passive device biasing the anode electrode away from the electrolyte and an active mechanism which, in operation, overcomes the biasing effect of the passive device to move the anode electrode into contact with the electrolyte.

65. The at least one electrochemical cell of claim 64 wherein the active mechanism receives power from the power source so that when the power source is connected to apply a voltage between the anode electrode and the cathode electrode the power source provides power to the active mechanism.

66. The at least one electrochemical cell of claim 54 wherein the lead dioxide electrocatalyst retains its β-lead dioxide crystalline form.

67. The at least one electrochemical cell of claim 66 further comprising an actuator for moving the anode electrode from the retracted position back to the initial position in response to one or more production conditions, wherein the acidic electrolyte is a proton exchange membrane, and wherein the one or mare production conditions includes a contact pressure of greater than 10 psig of the anode electrode with the proton exchange membrane.

68. At least one electrochemical cell including a cathode electrode, an anode electrode, an acidic electrolyte disposed between the anode electrode and the cathode electrode, and a power source for applying a voltage between the anode electrode and the cathode electrode, characterized in that the apparatus further comprises a mechanism to retract the anode electrode out of contact with the electrolyte in response to the absence of a current flowing through the electrochemical cell.

69. At least one electrochemical cell including a cathode electrode, an anode electrode, and an acidic electrolyte disposed between the anode electrode and the cathode electrode, and a power source for applying a voltage between the anode electrode and the cathode electrode, characterized in that the apparatus further comprises a passive mechanism biasing the anode electrode away from the electrolyte and an active mechanism which, when operative, overcomes the biasing effect of the passive mechanism to bring the anode electrode into contact with the electrolyte.

70. The at least one electrochemical cell of claim 69 wherein the active mechanism is adapted to be actuated when the power source is connected to apply the voltage between the electrodes.

71. The at least one electrochemical cell of claim 69, wherein the active mechanism is selected from electrical, hydraulic, pneumatic, piezoelectric, and combinations thereof.

72. The at least one electrochemical cell of claim 69, wherein the passive means is selected from a spring, gravity, hydraulic accumulator, pneumatic accumulator, and combinations thereof.

73. At least one electrochemical cell including a cathode electrode, an anode electrode, an acidic electrolyte disposed between the anode electrode and the cathode electrode, and a power source for applying a voltage between the anode electrode and the cathode electrode, characterized in that the apparatus further comprises a mechanism to retract the anode electrode out of contact with the electrolyte to interrupt a circuit incorporating the at least one electrochemical cell, thereby placing the at least one electrochemical cell in a standby condition.

74. The at least one electrochemical cell of claim 73, wherein the electrolyte is an ion exchange membrane.

75. The at least one electrochemical cell of claim 74, wherein the at least one electrochemical cell is a fuel cell.

76. The at least one electrochemical cell of claim 74, wherein the ion exchange membrane is a cation exchange membrane.

77. The at least one electrochemical cell of claim 73, wherein the mechanism to retract the anode is selected from a hydraulic actuator, a pneumatic actuator, manual mechanical means, piezo-electric means, electric motor means, or combinations thereof.

78. An electrochemical apparatus, comprising:
at least one electrochemical cell having first and second electrodes and electrolyte disposed between the first and second electrodes, wherein the one or more of the first and second electrodes includes material that is unstable or deactivates in the presence of the electrolyte without applying a voltage, a power source for applying a voltage between the first and second electrodes, and means for automatically retracting one or more of the first and second electrodes out of contact with the electrolyte.

79. The electrochemical apparatus of claim 78, wherein the means for automatically retracting is passive.

80. The electrochemical apparatus of claim 79, wherein the passive means for automatically retracting is a stored energy device.

81. The electrochemical apparatus of claim 80, wherein the stored energy device is selected from a spring, gravity, hydraulic accumulator, pneumatic accumulator, or combinations thereof.

82. The electrochemical apparatus of claim 78, wherein the electrolyte is an ion exchange membrane.

83. The electrochemical apparatus of claim 82, wherein the ion exchange membrane is a cation exchange membrane.

84. The electrochemical apparatus of claim 78, wherein the material is lead dioxide.

85. The electrochemical apparatus of claim 84, characterized in that the lead dioxide maintains its activity during repetitive cycling of the power source.

86. The electrochemical apparatus of claim 78, further comprising:

a pump for delivering water to the at least one electrochemical cell, wherein the means for retracting is a hydraulic actuator in fluid communication with the water.

87. The electrochemical apparatus of claim 86, further comprising means for introducing ozone into a separate system.

88. The electrochemical apparatus of claim 87, wherein the ozone comprises dissolved ozone in water, an ozone/oxygen gas stream, or combinations thereof.

89. The electrochemical apparatus of claim 78, wherein the electrolyte and one of the electrodes are stationary.

90. The electrochemical apparatus of claim 89, wherein the electrolyte is an ion exchange membrane.

91. The electrochemical apparatus of claim 90, wherein the stationary electrode is a cathode.

92. The electrochemical apparatus of claim 78, wherein the at least one electrochemical is a plurality of electrochemical cells.

93. The electrochemical apparatus of claim 92, wherein the plurality of electrochemical cells form a stack of electrochemical cells.

94. The electrochemical apparatus of claim 78, further comprising:

a lead-containing catalyst disposed on one or more of the first and second electrodes; and a lead removal device in fluid communication with the at least one electrochemical cell.

95. The electrochemical apparatus of claim 94, wherein the lead removal device contains a material known to bind or adsorb lead ions, particulates or colloidal species.

96. The electrochemical apparatus of claim 95, wherein the material is selected from a zeolite, alumina, silica, or mixtures thereof.

97. The electrochemical apparatus of claim 78, wherein the one or more of the first and second electrodes are retracted out of contact with the electrolyte when no voltage is being applied between the first and second electrodes.

98. The electrochemical apparatus of claim 78, wherein the means for retracting the one or more electrodes further comprises a guide member to align the electrodes.

99. The electrochemical apparatus of claim 78, wherein the means for retracting the electrodes is coupled to the one or more of the first and second electrodes by a positioning rod.

100. The electrochemical apparatus of claim 99, further comprising an electrode chamber having a liquid impermeable diaphragm sealing the chamber and moving along with the positioning rod.

101. The electrochemical apparatus of claim 78, further comprising:

means for positioning the first and second electrodes in contact with the electrolyte.

102. The electrochemical apparatus of claim 101, wherein the electrolyte is an ion exchange membrane, and wherein the first electrode is coupled to the means for positioning and the first electrode has an electrocatalyst formed only on surfaces of the first electrode that are disposed to make contact with the ion exchange membrane.

103. The electrochemical apparatus of claim 101, wherein the second electrode is stationary.

104. The electrochemical apparatus of claim 103, wherein the ion exchange membrane is secured onto the second electrode.

105. The electrochemical apparatus of claim 101, wherein the means for positioning is selected from a hydraulic actuator, a pneumatic actuator, manual mechanical means, piezo-electric means, electric motor means, or combinations thereof.

106. The electrochemical apparatus of claim 101, further comprising:

a pump for delivering water to the at least one electrochemical cell, wherein the means for positioning is a hydraulic actuator in fluid communication with the water.

107. The electrochemical apparatus of claim 101, wherein the means for positioning provides a compressive force against the ion exchange membrane generally greater than 15 psig.

108. The electrochemical apparatus of claim 101, wherein the compressive force is between 5 and 10 psig.

109. The electrochemical apparatus of claim 101, wherein the means for retracting overcomes the means for positioning when the power source is off.

110. The electrochemical apparatus of claim 101, wherein the means for positioning overcomes the means for retracting when the power source is on.

111. The electrochemical apparatus of claim 101, wherein the means for positioning the electrodes further comprises a guide member to align the electrodes.

112. The electrochemical apparatus of claim 101, wherein the means for positioning the electrodes is coupled to the one or more of the first and second electrodes by a positioning rod.

113. The electrochemical apparatus of claim 112, further comprising an electrode chamber having a liquid impermeable diaphragm sealing the chamber and moving along with the positioning rod.

114. The electrochemical apparatus of claim 112, wherein the positioning rod comprises an electronic conductor communicating between a voltage source and the one or more of the first and second electrodes.

115. The electrochemical apparatus of claim 101, further comprising a water reservoir in fluid communication with an inlet to the pump and in fluid communication with an outlet from the at least one electrochemical cell.

116. The electrochemical apparatus of claim 115, further comprising a recirculation conduit from an outlet of the pump back to the water reservoir.

117. The electrochemical apparatus of claim 116, further comprising means for apportioning the amount of water pumped to the at least one electrochemical cell and the amount of water recirculated back to the water reservoir.

118. The electrochemical apparatus of claim 101, further comprising an ion exchange bed disposed upstream of the at least one electrochemical cell.

119. The electrochemical apparatus of claim 118, further comprising an ozone destruct catalyst upstream of the ion exchange bed.

120. The electrochemical apparatus of claim 101, wherein the at least one electrochemical cell is a fuel cell.

121. An electrochemical apparatus, comprising:
at least one electrochemical cell having first and second electrodes and electrolyte disposed between the first and second electrodes,
a power source for applying a voltage between the first and second electrodes,
a pump for delivering water to the at least one electrochemical cell, and
means for automatically retracting one or more of the first and second electrodes out of contact with the electrolyte, and
a hydraulic actuator in fluid communication with the water for positioning the one or more electrodes in contact with the electrolyte.

122. The electrochemical apparatus of claim 121, wherein the means for automatically retracting is passive.

123. The electrochemical apparatus of claim 122, wherein the passive means for automatically retracting is a stored energy device.

124. The electrochemical apparatus of claim 123, wherein the stored energy device is selected from a spring, gravity, hydraulic accumulator, pneumatic accumulator, or combinations thereof.

125. The electrochemical apparatus of claim 121, wherein the electrolyte is an ion exchange membrane.

126. The electrochemical apparatus of claim 125, wherein the ion exchange membrane is a cation exchange membrane.

127. The electrochemical apparatus of claim 121, wherein the one or more of the first and second electrodes includes material that is unstable or deactivates in the presence of the electrolyte without applying a voltage.

128. The electrochemical apparatus of claim 127, wherein the material is lead dioxide.

129. The electrochemical apparatus of claim 128, characterized in that the lead dioxide maintains its activity during repetitive cycling of the power source.

130. The electrochemical apparatus of claim 121, wherein the electrolyte and one of the electrodes are stationary.

131. The electrochemical apparatus of claim 130, wherein the electrolyte is an ion exchange membrane.

132. The electrochemical apparatus of claim 131, wherein the stationary electrode is a cathode.

133. The electrochemical apparatus of claim 121, wherein the at least one electrochemical cell is a plurality of electrochemical cells.

134. The electrochemical apparatus of claim 133, wherein the plurality of electrochemical cells forms a stack.

135. The electrochemical apparatus of claim 121, wherein the one or more of the first and second electrodes are retracted out of contact with the electrolyte when no voltage is being applied between the first and second electrodes.

136. The electrochemical apparatus of claim 121, wherein the means for retracting the one or more electrodes further comprises a guide member to align the electrodes.

137. The electrochemical apparatus of claim 121, wherein the means for retracting the electrodes is coupled to the one or more of the first and second electrodes by a positioning rod.

138. The electrochemical apparatus of claim 137, further comprising an electrode chamber having a liquid impermeable diaphragm sealing the chamber and moving along with the positioning rod.

139. The electrochemical apparatus of claim 121, further comprising means for introducing ozone into a separate system.

140. The electrochemical apparatus of claim 139, wherein the ozone comprises dissolved ozone in water, an ozone/oxygen gas stream, or combinations thereof.

141. The electrochemical apparatus of claim 121, further comprising:
means for positioning the first and second electrodes in contact with the electrolyte.

142. The electrochemical apparatus of claim 141, wherein the electrolyte is an ion exchange membrane, and wherein the first electrode is coupled to the means for positioning and the first electrode has an electrocatalyst formed only on surfaces of the first electrode that are disposed to make contact with the ion exchange membrane.

143. The electrochemical apparatus of claim 142, wherein the second electrode is stationary.

144. The electrochemical apparatus of claim 143, wherein the ion exchange membrane is secured onto the second electrode.

145. The electrochemical apparatus of claim 141, wherein the means for positioning is selected from a hydraulic actuator, a pneumatic actuator, manual mechanical means, piezo-electric means, electric motor means, or combinations thereof.

146. The electrochemical apparatus of claim 141, wherein the means for positioning provides a compressive force against the ion exchange membrane generally greater than 15 psig.

147. The electrochemical apparatus of claim 141, wherein the compressive force is between 5 and 100 psig.

148. The electrochemical apparatus of claim 141, wherein the means for retracting overcomes the means for positioning when the power source is off.

149. The electrochemical apparatus of claim 141, wherein the means for positioning overcomes the means for retracting when the power source is on.

150. The electrochemical apparatus of claim 141, wherein the means for positioning the electrodes further comprises a guide member to align the electrodes.

151. The electrochemical apparatus of claim 141, wherein the means for positioning the electrodes is coupled to the one or more of the first and second electrodes by a positioning rod.

152. The electrochemical apparatus of claim 151, further comprising an electrode chamber having a liquid impermeable diaphragm sealing the chamber and moving along with the positioning rod.

153. The electrochemical apparatus of claim 151, wherein the positioning rod comprises an electronic conductor communicating between a voltage source and the one or more of the first and second electrodes.

154. The electrochemical apparatus of claim 141, further comprising a water reservoir in fluid communication with an inlet to the pump and in fluid communication with an outlet from the at least one electrochemical cell.

155. The electrochemical apparatus of claim 154, further comprising a recirculation conduit from an outlet of the pump back to the water reservoir.

156. The electrochemical apparatus of claim 155, further comprising means for apportioning the amount of water pumped to the at least one electrochemical cell and the amount of water recirculated back to the water reservoir.

157. The electrochemical apparatus of claim 141, wherein the at least one electrochemical cell is a fuel cell.

158. An electrochemical apparatus, comprising:
- a plurality of electrochemical cells, each electrochemical cell having first and second electrodes and electrolyte disposed between the first and second electrodes,
- a power source for applying a voltage between the first and second electrodes, and
- means for automatically retracting one or more of the first and second electrodes out of contact with the electrolyte.

159. The electrochemical apparatus of claim 158, wherein the means for automatically retracting is passive.

160. The electrochemical apparatus of claim 159, wherein the passive means for automatically retracting is a stored energy device.

161. The electrochemical apparatus of claim 160, wherein the stored energy device is selected from a spring, gravity, hydraulic accumulator, pneumatic accumulator, or combinations thereof.

162. The electrochemical apparatus of claim 158, wherein the one or more of the first and second electrodes includes material that is unstable or deactivates in the presence of the electrolyte without applying a voltage.

163. The electrochemical apparatus of claim 162, wherein the material is lead dioxide.

164. The electrochemical apparatus of claim 163, characterized in that the lead dioxide maintains its activity during repetitive cycling of the power source.

165. The electrochemical apparatus of claim 158, wherein the electrolyte and one of the electrodes are stationary.

166. The electrochemical apparatus of claim 165, wherein the electrolyte is an ion exchange membrane.

167. The electrochemical apparatus of claim 166, wherein the stationary electrode is a cathode.

168. The electrochemical apparatus of claim 166, wherein the ion exchange membrane is a cation exchange membrane.

169. The electrochemical apparatus of claim 158, wherein the one or more of the first and second electrodes are retracted out of contact with the electrolyte when no voltage is being applied between the first and second electrodes.

170. The electrochemical apparatus of claim 158, wherein the means for retracting the one or more electrodes further comprises a guide member to align the electrodes.

171. The electrochemical apparatus of claim 158, wherein the means for retracting the electrodes is coupled to the one or more of the first and second electrodes by a positioning rod.

172. The electrochemical apparatus of claim 171, further comprising an electrode chamber having a liquid impermeable diaphragm sealing the chamber and moving along with the positioning rod.

173. The electrochemical apparatus of claim 158, further comprising:
- means for positioning the first and second electrodes in contact with the electrolyte.

174. The electrochemical apparatus of claim 173, wherein the electrolyte is an ion exchange membrane, and wherein the first electrode is coupled to the means for positioning and the first electrode has an electrocatalyst formed only on surfaces of the first electrode that are disposed to make contact with the ion exchange membrane.

175. The electrochemical apparatus of claim 174, wherein the second electrode is stationary.

176. The electrochemical apparatus of claim 174, wherein the ion exchange membrane is secured onto the second electrode.

177. The electrochemical apparatus of claim 173, wherein the means for positioning is selected form a hydraulic actuator, a pneumatic actuator, manual mechanical means, piezo-electric means, electric motor means, or combinations thereof.

178. The electrochemical apparatus of claim 173, further comprising:
- a pump for delivering water to the at least one electrochemical cell, wherein the means for positioning is a hydraulic actuator in fluid communication with the water.

179. The electrochemical apparatus of claim 173, wherein the means for positioning provides a compressive force against the ion exchange membrane generally greater than 15 psig.

180. The electrochemical apparatus of claim 173, wherein the compressive force is between 5 and 100 psig.

181. The electrochemical apparatus of claim 173, wherein the means for retracting overcomes the means for positioning when the power source is off.

182. The electrochemical apparatus of claim 173, wherein the means for positioning overcomes the means for retracting when the power source is on.

183. The electrochemical apparatus of claim 173, wherein the means for positioning the electrodes further comprises a guide member to align the electrodes.

184. The electrochemical apparatus of claim 173, wherein the means for positioning the electrodes is coupled to the one or more of the first and second electrodes by a positioning rod.

185. The electrochemical apparatus of claim 184, further comprising an electrode chamber having a liquid impermeable diaphragm sealing the chamber and moving along with the positioning rod.

186. The electrochemical apparatus of claim 184, wherein the positioning rod comprises an electronic conductor communicating between a voltage source and the one or more of the first and second electrodes.

187. The electrochemical apparatus of claim 173, further comprising a water reservoir in fluid communication with an inlet to the pump and in fluid communication with an outlet from the at least one electrochemical cell.

188. The electrochemical apparatus of claim 187, further comprising a recirculation conduit from an outlet of the pump back to the water reservoir.

189. The electrochemical apparatus of claim 188, further comprising means for apportioning the amount of water pumped to the at least one electrochemical cell and the amount of water recirculated back to the water reservoir.

190. The electrochemical apparatus of claim 173, wherein the at least one electrochemical cell is a fuel cell.

191. The electrochemical apparatus of claim 158, wherein the plurality of electrochemical cells form a stack of electrochemical cells.

* * * * *